United States Patent
Yokoyama et al.

(10) Patent No.: US 10,314,301 B2
(45) Date of Patent: Jun. 11, 2019

(54) METHOD OF PRESERVING CELLS

(71) Applicant: SYSMEX CORPORATION, Kobe-shi, Hyogo (JP)

(72) Inventors: Koji Yokoyama, Kobe (JP); Noriko Oka, Kobe (JP); Masakatsu Morita, Nagoya (JP); Yuka Yamamoto, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 15/650,347

(22) Filed: Jul. 14, 2017

(65) Prior Publication Data

US 2017/0318801 A1 Nov. 9, 2017

Related U.S. Application Data

(63) Continuation-in-part of application No. PCT/JP2016/069280, filed on Jun. 29, 2016.

(30) Foreign Application Priority Data

Jun. 30, 2015 (JP) .................................. 2015-131552
Feb. 29, 2016 (JP) .................................. 2016-037266

(51) Int. Cl.
*A01N 1/02* (2006.01)
*C12N 1/00* (2006.01)
*C12N 1/04* (2006.01)
*C12Q 1/04* (2006.01)
*C12Q 1/68* (2018.01)
*G01N 1/30* (2006.01)
*C12N 11/16* (2006.01)
*G01N 33/48* (2006.01)
*G01N 33/50* (2006.01)

(52) U.S. Cl.
CPC .............. *A01N 1/021* (2013.01); *C12N 1/00* (2013.01); *C12N 1/04* (2013.01); *C12N 11/16* (2013.01); *C12Q 1/04* (2013.01); *C12Q 1/68* (2013.01); *G01N 1/30* (2013.01); *G01N 33/48* (2013.01); *G01N 33/50* (2013.01); *G01N 2001/305* (2013.01)

(58) Field of Classification Search
CPC . C12N 1/00; C12N 1/04; C12N 11/16; C12Q 1/04; C12Q 1/68; G01N 33/48; G01N 33/50; G01N 1/30; G01N 2001/305; A01N 1/021
See application file for complete search history.

(56) References Cited

U.S. PATENT DOCUMENTS

| 5,256,571 | A | 10/1993 | Hurley et al. |
| 7,291,455 | B2 | 11/2007 | Lorincz et al. |
| 2006/0078872 | A1 | 4/2006 | Taguchi et al. |
| 2006/0088814 | A1 | 4/2006 | Hecht et al. |
| 2009/0091746 | A1 | 4/2009 | Fukuda et al. |
| 2009/0233269 | A1 | 9/2009 | Linder et al. |

FOREIGN PATENT DOCUMENTS

| CN | 102258003 A | 11/2011 |
| EP | 0083286 A2 | 7/1983 |
| JP | 2011-250758 A | 12/2011 |

OTHER PUBLICATIONS

"pH". The Macmillan Encyclopedia (2003), 1 page. (Year: 2003).*
International Search Report for PCT/JP2016/069280 dated Sep. 13, 2016 [PCT/ISA/210].
Written Opinion for PCT/JP2016/069280 dated Sep. 13, 2016 [PCT/ISA/237].
Zhang Yaming et al; "Determination of Heat of Dilution of $CaCl_2/C_2H_5OH$—$H_2O$ Solution," Journal of Nanjing Institute of Chemical Technology, vol. 13, No. 4, Oct. 1991 (21 pages total).

* cited by examiner

*Primary Examiner* — Sean C. Barron
(74) *Attorney, Agent, or Firm* — Sughrue Mion, PLLC

(57) ABSTRACT

The present invention relates to a method of preserving cells in a cell preservative solution. The cell preservative solution comprises a lower alcohol having 1 to 6 carbon atoms and a divalent metal ion in an aqueous solvent, wherein the concentration of the divalent metal ion is from about 6 mmol/L to about 82 mmol/L.

20 Claims, 17 Drawing Sheets

Fluorescence area

Fig. 8A

METHOD OF PRESERVING CELLS

CROSS REFERENCE TO RELATED APPLICATIONS

This application claims priority from prior Japanese Patent Application No. 2015-131552, filed on Jun. 30, 2015, entitled "CELL PRESERVATIVE SOLUTION, USE OF SAME, AND METHOD OF PRODUCING CELL PRESERVATIVE SOLUTION", prior Japanese Patent Application No. 2016-037266, filed on Feb. 29, 2016, entitled "CELL PRESERVATIVE SOLUTION, USE OF SAME, AND METHOD OF PRODUCING CELL PRESERVATIVE SOLUTION", and PCT Application No. PCT/JP2016/069280 filed on Jun. 29, 2016 entitled "CELL PRESERVATIVE SOLUTION, USE OF SAME, AND METHOD OF PRODUCING CELL PRESERVATIVE SOLUTION", the entire contents of which are incorporated herein by reference.

TECHNICAL FIELD

The present invention relates to a cell preservative solution. Further, the present invention relates to a method of preserving cells, a method of preparing fixed cells, and a method of analyzing cells using a cell preservative solution. Furthermore, the present invention relates to a method of producing a cell preservative solution.

BACKGROUND ART

When analyzing cells, the cells are stored before being subjected to analysis. For example, when analyzing cells extracted from the living body, it is necessary to appropriately store the cells for the duration of the period from the time of cell extraction until the time of cell analysis because the cells separated from the living body begin to autolyze.

U.S. Pat. No. 5,256,571 describes that cells are stored in a cell preservative solution before analysis. Example 5 of U.S. Pat. No. 5,256,571 discloses that the cell preservative solution contains 1 mM magnesium acetate, 2 mM calcium acetate, 10 mM potassium chloride, 0.1% sodium chloride, and 20% methanol.

SUMMARY

The present invention provides a cell preservative solution containing a lower alcohol having 1 to 6 carbon atoms and a divalent metal ion in an aqueous solvent, wherein the concentration of the divalent metal ion is from about 6 mmol/L to about 82 mmol/L.

The present invention provides a method of preserving cells, comprising allowing the cells to be immersed in vitro in the cell preservative solution.

The present invention provides a method of producing a cell preservative solution, comprising mixing a lower alcohol having 1 to 6 carbon atoms and a divalent metal ion in an aqueous solvent, wherein the concentration of the divalent metal ion in the cell preservative solution is from about 6 mmol/L to about 82 mmol/L.

The present invention provides a method of preparing fixed cells, comprising contacting cells in vitro with the cell preservative solution so as to make the cells fixed.

The present invention provides a method of analyzing cells comprising the steps of: contacting cells in vitro with the cell preservative solution so as to make the cells fixed; and analyzing nucleic acids in the fixed cells which are obtained in the step.

BRIEF DESCRIPTION OF DRAWINGS

FIG. 8A shows fluorescence area histograms obtained by analyzing HeLa cells stored in cell preservative solutions having various methanol concentrations under predetermined conditions with the flow cytometer.

DESCRIPTION OF EMBODIMENTS

[1. Cell Preservative Solution]

Figure 1:
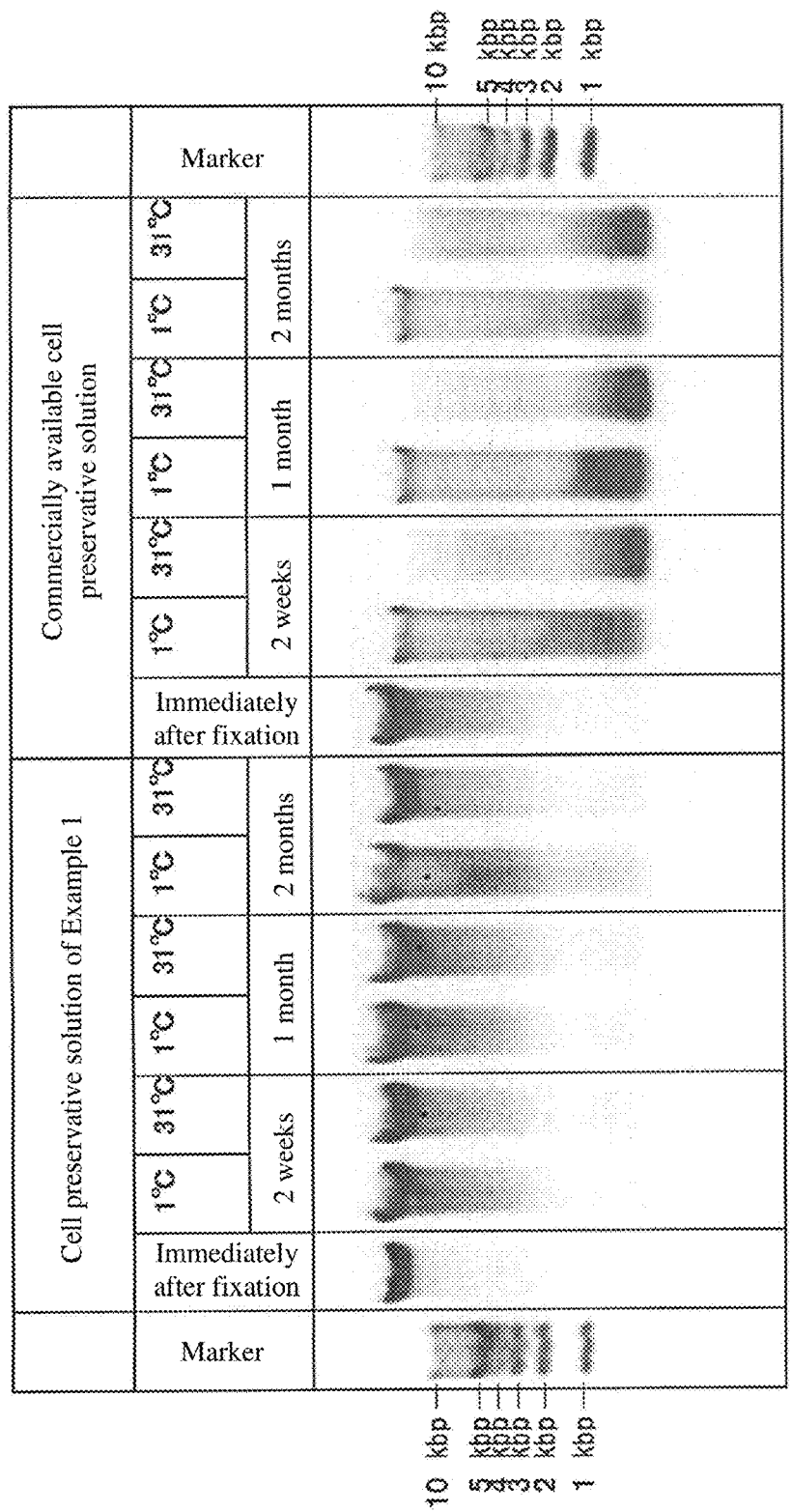
FIG. 1 is a photograph of agarose gel electrophoresis of DNA extracted from HeLa cells stored in a cell preservative solution of an embodiment of the present invention or a commercially available cell preservative solution under predetermined conditions.

The cell preservative solution of the embodiment comprises a lower alcohol having 1 to 6 carbon atoms and a divalent metal ion in an aqueous solvent, wherein the concentration of the divalent metal ion is from about 6 mmol/L to about 82 mmol/L.

The lower alcohol having 1 to 6 carbon atoms (hereinafter simply referred to as "lower alcohol") is not particularly limited as long as it can be mixed with water in an optional proportion at ordinary temperature (25° C.). Examples thereof include methanol, ethanol, n-propanol, isopropanol, n-butanol, isobutanol, sec-butanol, tert-butanol, n-amyl alcohol, isoamyl alcohol, sec-amyl alcohol, tert-amyl alcohol, 1-ethyl-1-propanol, 2-methyl-1-butanol, n-hexanol, and cyclohexanol. Among them, methanol or ethanol is preferred, and methanol is particularly preferred from the viewpoint of effects involved in the storage and fixation of cells (dehydration and coagulation of protein).

In the embodiment, only one kind of lower alcohol or two or more kinds of lower alcohol may be used. Two or more kinds of alcohol may be mixed in an optional proportion. For example, a mixed alcohol obtained by mixing methanol and ethanol in an optional proportion may be used as the cell preservative solution.

The concentration of the lower alcohol in the cell preservative solution can be appropriately set according to the storage period of cells, the method of analyzing cells or the like. A too-low concentration (for example, in the case where the concentration is lower than about 20% by volume) makes the stable storage of cells difficult. A too-high concentration (for example, in the case where the concentration is higher than about 60% by volume) may cause excessive fixation of cells. In the embodiment, the concentration of the lower alcohol is usually from about 20% by volume to about 60% by volume, preferably from about 30% by volume to about 50% by volume, and particularly preferably from about 40% by volume to about 45% by volume. In the further embodiment, the concentration of the lower alcohol is from 20% by volume to 60% by volume, preferably from 30% by volume to 50% by volume, and particularly preferably from 40% by volume to 45% by volume. The lower alcohol is contained at the above concentration so that the cells can be stably stored. Further, the bacteriostatic effect or bactericidal effect can also be expected. It should be noted herein that "% by volume" is also indicated by "v/v %" or "vol %."

The divalent metal ion is not particularly limited as long as it does not affect the maintenance of the form and constituent of cells, and may be selected from, for example, metal ions which are added to a cell culture medium. In the embodiment, examples of the divalent metal ion include a magnesium ion, a calcium ion, a zinc ion, an iron (II) ion, a copper ion, a strontium ion, and a molybdenum ion. Among them, the metal ions of the Group II element are preferred. As the metal ion of the Group II element, a magnesium ion and a calcium ion are particularly preferred. In the embodiment, only one kind of divalent metal ion or two or more kinds of divalent metal ions may be used.

In the embodiment, the divalent metal ion in the cell preservative solution is preferably supplied from a divalent metal compound soluble in an aqueous solvent. Examples of the compound include inorganic or organic acid salts of divalent metals. Examples of the inorganic acid salts of divalent metals include salts of inorganic acids (such as hydrochloric acid, sulfuric acid, nitric acid, perchloric acid, hydrobromic acid, and hydriodic acid) with divalent metals. Examples of the organic acid salts of divalent metals include salts of organic acids (such as acetic acid, citric acid, ascorbic acid, and oxalic acid) with divalent metals. Among them, the inorganic acid salts of divalent metals are preferred. Examples thereof include magnesium chloride, magnesium sulfate, and calcium chloride. In the embodiment, the divalent metal compound may be an anhydride or a hydrate.

With reference to the concentration of the divalent metal ion, the present inventors have found that, in a cell preservative solution containing a lower alcohol as a main component, the concentration of the divalent metal ion is set to a range of from about 6 mmol/L to about 82 mmol/L, whereby cells and nucleic acids in the cells can be stably stored in vitro during a predetermined period. In the embodiment, the concentration of the divalent metal ion may be from about 6 mmol/L to about 80 mmol/L, from about 6 mmol/L to about 60 mmol/L, from about 6 mmol/L to about 50 mmol/L, or from about 6 mmol/L to about 40 mmol/L. In another embodiment, the concentration of the divalent metal ion may be from about 10 mmol/L to about 80 mmol/L, from about 10 mmol/L to about 60 mmol/L, from about 10 mmol/L to about 50 mmol/L, or from about 10 mmol/L to about 40 mmol/L. In another embodiment, the concentration of the divalent metal ion may be from 6 mmol/L to 80 mmol/L, from 6 mmol/L to 60 mmol/L, from 6 mmol/L to 50 mmol/L, or from 6 mmol/L to 40 mmol/L. In another embodiment, the concentration of the divalent metal ion may be from 10 mmol/L to 80 mmol/L, from 10 mmol/L to 60 mmol/L, from 10 mmol/L to 50 mmol/L, or from 10 mmol/L to 40 mmol/L. In another embodiment, It should be noted herein that "mmol/L" is also indicated by "mM". In the embodiment, in the case where the divalent metal compound soluble in an aqueous solvent, particularly an inorganic acid salt of divalent metal, is dissolved in the cell preservative solution, the concentration of the divalent metal ion in the cell preservative solution may be expressed by the concentration of the compound.

The aqueous solvent can be mixed with a lower alcohol in an optional proportion at ordinary temperature (25° C.) and is not particularly limited as long as it does not affect the maintenance of the form and constituent of cells. Examples of the aqueous solvent include water, physiological saline, a buffer solution, an albumin solution, a dextran solution, a normal human or mammal serum solution, and any combination thereof.

The buffer solution is preferably used as the aqueous solvent. The buffer solution is not particularly limited as long as it is a buffer solution having a buffer action at a pH of from 6 to 8. Examples thereof include a good buffer solution, a phosphate buffer solution (PBS), an imidazole buffer solution, and a triethanolamine hydrochloride buffer solution (TEA). Examples of the good buffer solution include aqueous solutions of buffers such as PIPES, MES, Bis-Tris, ADA, Bis-Tris-Propane, ACES, MOPS, MOPSO, BES, TES, HEPES, HEPPS, Tricine, Tris, Bicine, and TAPS. In the case of using aqueous solvents other than the buffer solution, any buffers used in the above buffer solutions may be added to the cell preservative solution.

In the embodiment, the pH of the cell preservative solution may be in a range suitable for storage of cells, and is usually in a range of from about 6 to about 8, and preferably in a range of from about 6.4 to about 7. In the further embodiment, the pH of the cell preservative solution is in a range of from 6 to 8 and preferably in a range of from 6.4 to 7. The osmotic pressure of the cell preservative solution is not particularly limited as long as it does not inhibit the storage of cells, and it may be physiologically isotonic.

If necessary, the cell preservative solution of the embodiment may contain an additive in the aqueous solvent, in addition to the lower alcohol and the divalent metal ion. The additive is not particularly limited as long as it does not inhibit the fixation, storage and analysis of cells. Examples thereof include known substances such as inorganic salts (e.g., sodium chloride, potassium chloride), saccharides (e.g., glucose, trehalose), preservatives (e.g., sodium azide, phenylmethanesulfonyl fluoride), protein stabilizers (e.g., bovine serum albumin), antifoaming agents (e.g., ethylene glycol), antibiotics (e.g., penicillin, streptomycin), and antifungal agents (e.g., amphotericin B).

The cells to be stored in the cell preservative solution of the embodiment are not particularly limited and may be, for example, cells of multicellular organisms, cells of unicellular organisms or cultured cell lines. The cells of multicellular organisms may be cells extracted from the living body or may be cells extracted from the dead body. Examples of the cells of multicellular organisms include cells extracted from mammals such as human. Specific examples thereof include cervical cells, cells in the uterine corpus, oral cells, mammary glandular cells, thyroid cells, cells in urine, cells in the sputum, bronchial brushing cells, cells in the peritoneal washing, and cells in the coelomic fluid. Further, the cells may be cells contained in the tissues extracted from mammals such as human. The extracted tissues may be normal tissues or tissues including lesion sites. Examples of the cells contained in the extracted tissues include primary cultured cells, umbilical vein endothelial cells in the umbilical cord, and tumor cells contained in tumor tissues extracted by operation or biopsy. The cells may be protozoans such as trichomonas or fungi such as *Candida*. The cells may be cells prepared artificially in vitro such as stem cells or iPS cells. The properties of the cells are not particularly limited and the cells may be normal cells, immortal cells, cancer cells or the like.

Figure 12:
FIG. 12 is a schematic view showing an example of the cell preservative solution accommodated in a container.

FIG. 12 shows an example of the appearance of the cell preservative solution of the embodiment. In the figure, 11 denotes a cell preservative solution accommodating container. The cell preservative solution accommodating container of the embodiment may be accommodated in a box and then provided for a user. This box may include a package insert that describes the method of using the cell preservative solution. Further, when the cell preservative solution of the embodiment is provided for the storage of cervical cells, the box may include a cell sampler for extraction of cells from the uterine cervix (e.g., a swab, a brush).

[2. Method for Producing Cell Preservative Solution]

Hereinafter, the method of producing a cell preservative solution of the embodiment (hereinafter, also simply referred to as "production method") will be described. The production method of the embodiment is the method of producing a cell preservative solution, comprising mixing a lower alcohol having 1 to 6 carbon atoms and a divalent metal ion in an aqueous solvent so that the concentration of the divalent metal ion is from about 6 mmol/L to about 82 mmol/L. It should be noted that the concentrations and kinds of the lower alcohol having 1 to 6 carbon atoms and the divalent metal ion are the same as those described about the cell preservative solution.

In the embodiment, the divalent metal compound soluble in an aqueous solvent (hereinafter also simply referred to as "metal compound") is preferably used as the divalent metal ion. It should be noted that this compound is the same as that described about the cell preservative solution. The metal compound used for the production method of the embodiment may be in the form of a solution, or may have a solid shape (e.g., a powder or a crystal).

The lower alcohol used for the production method of the embodiment may be absolute alcohol. Alternatively, as long as the lower alcohol can be controlled to have the above concentration, it may be hydrous alcohol.

In the embodiment, there is no particular limitation as to the order of adding the lower alcohol and the metal compound as the divalent metal ion to the aqueous solvent. For example, the metal compound may be mixed after mixing the lower alcohol and the aqueous solvent, or the lower alcohol may be added after mixing the metal compound and the aqueous solvent. Further, the lower alcohol and the divalent metal ion may be mixed in the aqueous solvent substantially at the same time. The mixing conditions are not particularly limited, and the mixing may be performed, for example, at ordinary temperature under normal pressure (e.g., at 25° C. under a pressure of 1 atm).

In the embodiment, the pH of the mixture obtained as described above is preferably adjusted to a range of from about 6 to about 8, particularly a range of from about 6.4 to about 7, using an alkali such as sodium hydroxide or an acid such as hydrochloric acid. In the further embodiment, it is preferable that the pH of the mixture is adjusted to a range of from 6 to 8, particularly a range of from 6.4 to 7.

In the embodiment, in addition to the lower alcohol and the divalent metal ion, an additive may be added, if necessary, It should be noted that the additive is the same as that described about the cell preservative solution.

[3. Method for Preserving Cells using Cell Preservative Solution]

The method of preserving cells (hereinafter, simply referred to as "preservation method") of the embodiment will be described hereinbelow. The preservation method of the embodiment includes allowing the cells to be immersed in vitro in the cell preservative solution of the embodiment.

The cells used in the preservation method of the embodiment are the same as those described above.

In the embodiment, cells are immersed in vitro in a sufficient amount (e.g., an amount that is 100 to 1000 times the volume of cells) of the cell preservative solution, thereby allowing the cells to be fixed. Thereafter, the cells can be stored during a predetermined period. If necessary, the cells after being immersed in the cell preservative solution may be stirred to the extent that the cells are not damaged so as to give a suspension. Before being immersed in the cell preservative solution, the cells may be rinsed with PBS or the like. When cells are extracted from the living body, the cells begin to autolyze immediately, resulting in deformation of cells and nuclear structures and degradation and modification of cell contents such as nucleic acid and protein. Thus, the cells are preferably immersed in the cell preservative solution within 1 minute at the latest after the extraction. A preservation container is not particularly limited as long as it is a container which can be sealed with a lid, a seal or the like. Examples thereof include a vial, a test tube, a microtube, a microplate, a dish, and a bottle.

The temperature when immersing the cells in the cell preservative solution (temperature when contacting the cells with the cell preservative solution) is preferably 35° C. or lower, more preferably 32° C. or lower, and still more preferably 30° C. or lower. The lower limit of the temperature when immersing the cells in the cell preservative solution is not particularly limited as long as the subsequent analysis is not affected by freezing of the cell preservative solution and the cells. For example, the lower limit of the temperature may be 1° C. or higher or 2° C. or higher. The preservation method of the embodiment may include a step of contacting cells with the cell preservative solution at the above temperature so as to make the cells fixed.

The storage temperature of the cells is preferably 35° C. or lower, more preferably 32° C. or lower, and still more preferably 30° C. or lower. In the case where the cells are stored in the cell preservative solution of the embodiment, the nucleic acids of the cells can be stably maintained in the cases of not only chilled storage but also room-temperature storage. The lower limit of the storage temperature is not particularly limited as long as the subsequent analysis is not affected by freezing of the cell preservative solution and the cells. For example, the lower limit of the storage temperature may be 1° C. or higher or 2° C. or higher. The preservation method of the embodiment may include a step of storing cells in a cell preservative solution at the above temperature during a predetermined period. It should be noted that the temperature at the time of contact of the cells with the cell preservative solution and the storage temperature of the cells may be the same as or different from each other.

The cell preservative solution may be replaced during the storage period. Although the replacement frequency of the cell preservative solution is not particularly limited, the cell preservative solution may be replaced, for example, once per 90 days.

[4. Method of Preparing Fixed Cells using Cell Preservative Solution]

The method of preparing fixed cells of the embodiment (hereinafter, also simply referred to as "preparation method") will be described hereinbelow. The preparation method of the embodiment includes contacting cells in vitro with the cell preservative solution of the embodiment so as to make the cells fixed. It should be noted that the cells used in the preparation method of the embodiment are the same as those described in the method of preserving cells of the embodiment.

In the embodiment, contacting of cells with the cell preservative solution may be performed by immersing the cells in a sufficient amount (e.g., an amount that is 100 to 1000 times the volume of cells) of the cell preservative solution. Alternatively, contacting of cells with the cell preservative solution may be performed by placing the cells in an empty container and adding a sufficient amount of the cell preservative solution thereto. Before being contacted with the cell preservative solution, the cells may be rinsed with PBS or the like. The cells begin to autolyze immediately, thereby resulting in deformation of cells and nuclear structures and degradation and modification of cell contents such as nucleic acid and protein. Thus, the cells are preferably contacted with the cell preservative solution within 1 minute at the latest after the extraction. The container used for the contact is not particularly limited and examples thereof include a vial, a test tube, a microtube, a microplate, a dish, and a bottle. If necessary, the container may be sealed with a lid, a seal or the like.

In the preparation method of the embodiment, the cells contacted with the cell preservative solution are fixed by the effects of the lower alcohol contained in the cell preservative solution (dehydration and coagulation of protein). In the embodiment, the contact time of the cells with the cell preservative solution is not particularly limited as long as the cells are sufficiently fixed. The temperature conditions at the time of contact are the same as those described in the preservation method of the embodiment.

In the embodiment, the resulting fixed cells may be used directly or after being rinsed with PBS or the like, as specimens for desired analysis. Alternatively, the cells and the cell preservative solution may be stored in a state of being in contact with each other before being subjected to analysis. The storage conditions of the cells are the same as those described about the preservation method of the embodiment.

[5. Method of Analyzing Cells using Cell Preservative Solution]

The method of analyzing cells (hereinafter, simply referred to as "analytical method") of the embodiment will be described hereinbelow. In the analytical method of the embodiment, cells are first contacted in vitro with the cell preservative solution of the embodiment so as to make the cells fixed. The cells, the cell preservative solution, and the fixation of the cells are the same as those described above.

Subsequently, the nucleic acids in the resulting fixed cells are analyzed. In the embodiment, it is preferable to obtain information showing the amount of nucleic acids in nucleic acid analysis. The form of the information showing the amount of nucleic acids is not particularly limited and can be appropriately determined according to the method of obtaining the information. The information showing the amount of nucleic acids may be numerical information (e.g., a measured value), may be a diagram (e.g., a graph obtained based on the numerical information), or may be image information (e.g., a stained image, a gel electrophoresis photograph).

The nucleic acids in the fixed cells may be nucleic acids originally present in the cells or nucleic acids externally introduced by gene introduction, viral infection or the like. The kind of nucleic acids may be either DNA or RNA. In the embodiment, the nucleic acids in the fixed cells may be cDNA or cRNA synthesized from the nucleic acids extracted from the fixed cells.

In the embodiment, the method of analyzing the nucleic acids in the fixed cells may be selected from known methods in the art. Examples of the method include microscopic observation, flow cytometry, nucleic acid amplification assays (e.g., a PCR assay, an RT-PCR assay, a Real-Time PCR assay), hybridization assays (e.g., a Southern hybridization assay, a Northern hybridization assay), a microarray method, and a hybrid capture (HC) method (see Clavel C. et al., J. Clin. Pathol., vol. 51, p. 737-740 (1998)) (Clavel C. et al., J. Clin. Pathol., vol. 51, p. 737-740 (1998), which is incorporated herein by reference).

In the embodiment, it is preferable that a measurement sample is prepared from the fixed cells and then the sample is analyzed. The measurement sample may be prepared by disrupting the fixed cells or without disrupting the fixed cells. The preparation procedure for disrupting the fixed cells is, for example, a procedure for extracting nucleic acids from the fixed cells. The preparation procedure without disrupting the fixed cells is, for example, a procedure for staining nucleic acids in a state where the form of the fixed cells is maintained.

The method of extracting nucleic acids from cells as such is known in the art. When extracting DNA, for example, fixed cells are mixed with a lysate containing a surfactant (e.g., sodium cholate, sodium dodecyl sulfate). When extracting RNA, for example, fixed cells are mixed with a lysate containing guanidine thiocyanate and a surfactant. Then, the resulting mixture is subjected to physical process (e.g. stirring, homogenization, ultrasonic fragmentation) so as to allow nucleic acids contained in a biological sample to be free in the mixture, thereby achieving extraction of the nucleic acids. In this case, it is preferable that the mixture is centrifuged so as to precipitate cell debris and then the supernatant containing the free nucleic acids is used for analysis. Alternatively, the resulting supernatant may be purified by any known method in the art. The extraction and purification of the nucleic acids from the cells can also be performed using a commercially available kit.

The method of staining nucleic acids while maintaining the cell form as such is known in the art. For example, fixed cells are first contacted with a treatment solution containing a surfactant (e.g., Nonidet (registered trademark) P-40), Triton (registered trademark) X-100), so that a certain level of damage through which a nucleic acid staining dye can pass is given to a cell membrane. Then, the fixed cells after the treatment are contacted with a solution of the dye so that nucleic acids can be stained while the form of the fixed cells is maintained.

The dye for staining nucleic acid can be appropriately selected from known nucleic acid staining dyes according to the method of analyzing nucleic acids. For example, when a light microscope is used to obtain information, examples of the nucleic acid staining dye include hematoxylin, pyronin Y (pyronin G), and methyl green. Further, when a fluorescence microscope, a flow cytometer or the like is used to obtain information, it is preferable to use a fluorescent dye capable of staining nucleic acid as the nucleic acid staining dye. Examples of the fluorescent dye include propidium iodide, ethidium bromide, ethidium-acridine heterodimer, ethidium diazido, ethidium homodimer-1, ethidium homodimer-2, ethidium monoazide, Hoechst33342, Hoechst33258, 4',6-diamidino-2-phenylindole-dihydrochloride (DAPI), trimethylene bis[[3-[[4-[[(3-methylbenzothiazole-3-ium)-2-yl] methylene]-1,4-dihydroquinoline]-1-yl] propyl]dimethyl aminium]•tetraiodide (TOTO-1), 4-[(3-methylbenzothiazole-2(3H)-ylidene)methyl]-1-[3-(trimethylaminio)propyl] quinolinium diiodide (TO-PRO-1), N,N,N',N'-tetramethyl-N,N'-bis[3-[4-[3-[(3-methylbenzothiazole-3-ium)-2-yl]-2-propenylidene]-1,4-dihydroquinolin-1-yl] propyl]-1,3-propane diaminium•tetraiodide (TOTO-3), and 2-[3-[[1-[3-(trimethylaminio)propyl]-1,4-dihydroquinoline]-4-ylidene]-1-propenyl]-3-methylbenzothiazole-3-ium•diiodide (TO-PRO-3).

A measurement sample containing nucleic acids extracted from fixed cells is suitable for an analytical method of detecting a predetermined nucleic acid in the fixed cells (e.g., a nucleic acid amplification method, a hybridization method, a microarray method, an HC method). A measurement sample containing fixed cells whose nucleic acids are stained while the form of the fixed cells is maintained is suitable for an analytical method of obtaining information on nucleic acids in respective cells (e.g., microscopic observation, flow cytometry). In the embodiment, an appropriate measurement sample is prepared from fixed cells according to the purpose of analysis and the analysis may be performed.

When the nucleic acids in the fixed cells are analyzed by flow cytometry, it is preferable to perform the step of staining the nucleic acids in the fixed cells between the step of fixing cells and the step of obtaining information. The staining of the nucleic acids in the fixed cells is as described above. The nucleic acids in the stained and fixed cells are analyzed by suitably using a microscope, flow cytometry or the like. The intensity of staining of the cells by the nucleic acid staining dye is mainly dependent on the amount of intracellular nucleic acids. It should be noted that the structure of chromatin is involved in the intensity of staining (easiness for being stained) and the intensity of staining is assumed to be most dependent on the amount of nucleic acids. Therefore, the intensity of staining of the cells is measured with a microscope, flow cytometry or the like so that it is possible to obtain information showing the amount of nucleic acids. Specifically, when using flow cytometry, the stained and fixed cells are introduced into a flow cytometer and fluorescent signals from the cells are obtained. Based on the fluorescent signals, information showing the amount of nucleic acids can be obtained.

In the embodiment, as the analytical method based on flow cytometry, for example, the cell analyzer or the cell analyzing method described in, for example, U.S. Patent Application Publication No. 2009/0091746, may be used (U.S. Patent Application Publication No. 2009/0091746 is incorporated herein by reference). Specifically, a plurality of cells including "a measurement target cell" in U.S. Patent Application Publication No. 2009/0091746 are fixed in the cell preservative solution of the embodiment and the fixed cells can be analyzed with the cell analyzer or analyzed by the cell analyzing method.

In the measurement with a flow cytometer, a measurement sample containing the stained and fixed cells is introduced into a flow cell of the flow cytometer and the cells passing through the flow cell are irradiated with light, thereby obtaining optical information emitted from respective cells (fluorescent information and scattered light information).

In the embodiment, the fluorescent information is information (e.g., waveform, fluorescent intensity) obtained by emitting excitation light having an appropriate wavelength to respective cells stained with the fluorescent dye and measuring the excited fluorescence. The fluorescence is emitted from the nucleic acids in the cells stained with the fluorescent dye. Accordingly, the fluorescent information reflects the amount of the nucleic acids in the fixed cells. It should be noted that a light-receiving wavelength can be appropriately selected depending on the used fluorescent dye.

In the embodiment, scattered light information is not particularly limited as long as the light is scattered light which can be measured with a commercially available flow cytometer. For example, a scattered light pulse width and a scattered light intensity of scattered light such as forward scattered light (e.g., light receiving angle around 0 to 20 degrees) and side scattered light (light receiving angle around 90 degrees) can be used as scattered light information. In the art, it is known that the side scattered light reflects internal information such as nuclei or granules of cells and the forward scattered light reflects information on cell size.

In the embodiment, the light source of the flow cytometer is not particularly limited, and a light source having a wavelength suitable for excitation of the fluorescent dye is selected. For example, a red semiconductor laser, a blue semiconductor laser, an argon laser, a He—Ne laser or a mercury arc lamp is used. Particularly, since a semiconductor laser is very inexpensive as compared with a gas laser, which is thus preferable.

In the embodiment, with reference to the above optical information, characteristic parameters reflecting the amount of DNA contained in cells, the size of nuclei, the size of cells or the like are extracted by, for example, analyzing signal waveforms. Cancerous and atypical cells may be determined using those characteristic parameters.

In the analytical method of the embodiment, the step of analyzing nucleic acids in fixed cells may include a step of detecting a predetermined nucleic acid in the fixed cells. In this case, it is preferable to use a sample containing nucleic acids extracted from the fixed cells as the measurement sample.

In the embodiment, the predetermined nucleic acid is not particularly limited, and an optional nucleic acid of interest may be detected. The detection method is not particularly limited and is preferably a hybridization method using a polynucleotide that can be specifically hybridized to the predetermined nucleic acid (a probe or primer), a microarray method, an HC method, a nucleic acid amplification method or the like. Such a polynucleotide may be DNA or RNA. Further, those skilled in the art can appropriately design the polynucleotide corresponding to the base sequence of the predetermined nucleic acid.

The term "can be specifically hybridized to" used herein means that the polynucleotide as the probe or primer can be hybridized to the predetermined nucleic acid under stringent conditions. Here, the stringent conditions are conditions where the polynucleotide can be hybridized to the predetermined nucleic acid at a high detectable level, compared to nucleic acids other than the predetermined nucleic acid (e.g., at least more than twice the background). It should be noted that the stringent conditions are usually sequence-dependent and different in various environments. Generally, the stringent conditions are selected in such a manner that the thermal melting point (Tm) is lower by about 5° C. than the thermal melting point of a specific sequence at a specified ionic strength and pH. The Tm is a temperature at which 50% of the polynucleotide complementary to the base sequence of the predetermined nucleic acid is hybridized at equilibrium (depending on the specified ionic strength, pH, and the composition of nucleic acids).

In the embodiment, the probe may be labeled with any labeling substance known in the art. Examples of the labeling substance include radioactive substances such as $^{32}P$, $^{35}S$, $^{3}H$, and $^{125}I$; fluorescent substances such as fluorescein and Alexa Fluor (registered trademark); enzymes such as alkaline phosphatase and horseradish peroxidase; hapten such as 2,4-dinitrophenyl group, biotin, and avidin. When detecting nucleic acids by the HC method, anti-DNA/RNA hybrid antibodies are preferably labeled with these labeling substances. Further, when detecting nucleic acids by microarrays, nucleic acids in a measurement sample are preferably labeled with the above labeling substances.

In the embodiment, nucleic acids can be detected as follows. In the hybridization method, by detecting a signal from the labeled probe specifically hybridized to a predetermined nucleic acid, the predetermined nucleic acid can be detected. In the microarray method, when there is a labeled nucleic acid specifically hybridized to a probe disposed on the microarray, by detecting a signal from the labeled nucleic acid, the predetermined nucleic acid can be detected. It should be noted that the term "detecting a signal" used herein includes qualitatively detecting the presence or absence of a signal, quantifying a signal intensity, and semi-qualitatively detecting the signal intensity at a plurality of stages, such as "no signal", "weak signal" or "strong signal".

In the nucleic acid amplification method, the reaction solution after amplification using a primer complementary to the base sequence of a predetermined nucleic acid is subjected to gel electrophoresis, and the presence or absence of an amplified product is confirmed. When the amplified product is present, the predetermined nucleic acid can be detected. Alternatively, in the Real-Time PCR assay using a fluorescent substance which intercalates into DNA (e.g., SYBR (registered trademark) Green I) or a TaqMan (trademark) probe, by detecting a signal from the fluorescent substance or probe in the reaction solution after or during amplification, the predetermined nucleic acid can be detected.

In the HC method, a hybrid of a predetermined nucleic acid (DNA) and a RNA probe specifically hybridized to the nucleic acid is trapped by a solid-phased antibody and a labeled antibody and a signal from the labeled antibody is detected, whereby the predetermined nucleic acid can be detected.

In the embodiment, cells extracted from the uterine cervix are fixed in the cell preservative solution. As a predetermined nucleic acid, a human papilloma virus (HPV)-derived nucleic acid may be detected in the cells. Infection with HPV causes DNA of HPV to be incorporated into the genomic DNA of host cells. Thus, when the HPV-derived nucleic acid is detected in cells extracted from the uterine cervix of a subject, the subject can be determined to be infected with HPV.

HPV is classified into 100 or more kinds of subtypes. In the embodiment, the detection target HPV is not particularly limited and may be optionally selected from known subtypes. For example, a nucleic acid derived from high-risk-type HPV which is thought to have a high possibility of causing cervical cancer may be detected. Examples of the high-risk-type HPV include HPV-16, HPV-18, HPV-31, HPV-33, HPV-35, HPV-39, HPV-45, HPV-51, HPV-52, HPV-56, HPV-58, HPV-59, HPV-68, HPV-73, and HPV-82.

The method of detecting the HPV-derived nucleic acid may be appropriately selected from known detection methods. For example, the HPV-derived nucleic acid may be detected by the nucleic acid amplification method using a primer capable of amplifying the genomic DNA of the detection target HPV. Further, the HPV-derived nucleic acid may be detected by the hybridization method or the HC method using a probe that can be specifically hybridized to the genomic DNA of HPV. It should be noted that those skilled in the art can appropriately design a primer and a probe corresponding to the base sequence of the genomic DNA of HPV. In order to detect the HPV-derived nucleic acid, a commercially available HPV detection kit may be used.

The cells fixed in the cell preservative solution of the embodiment can be subjected to not only the method of analyzing nucleic acids but also the method of analyzing the size and form of cells, nuclei or the like. When analyzing the size and form of cells, nuclei or the like, for example, a flow cytometer and a microscope may be used.

When using the flow cytometer, scattered light information and fluorescent information are obtained by allowing cells with fluorescent-stained nuclei to pass through a flow cell and irradiating respective cells with light. Based on each information, abnormal cells can be detected. As the flow cytometer, for example, an apparatus described in U.S. Patent Application Publication No. 2015/0104786 may be used (U.S. Patent Application Publication No. 2015/0104786 is incorporated herein by reference). Further, a commercially available exfoliative cell analyzer: LC-1000 (Sysmex Corporation) may be used.

Further, a flow cytometer having an image pick-up function may be used. Respective cells flowing through the flow cell are imaged and a pathologist or the like observes the imaged cells, thereby allowing for detection of abnormal cells.

When using a microscope, for example, cells are analyzed in such a manner that cells fixed in the cell preservative solution of the embodiment are stained, the cells are smeared on a slide glass, and then the cells are observed with a microscope. In the microscopic observation, the pathologist or the like may observe the cells with the microscope. A stained image is photographed with a microscope having an image pick-up function and the pathologist or the like may observe the photographed image. The process of smearing the cells on the slide glass may be manually performed by the pathologist or the like, or may be automatically performed using a sample preparation apparatus. As the sample preparation apparatus, an apparatus described in U.S. Pat. No. 5,240,606 may be used (U.S. Pat. No. 5,240,606 is incorporated herein by reference). Further, a commercially available sample preparation apparatus such as a ThinPrep (registered trademark) processor may be used.

The present invention further includes use of the cell preservative solution for storing cells. Further, the present invention also includes use of the cell preservative solution for preparing fixed cells. Furthermore, the present invention also includes use of the cell preservative solution for analyzing cells. The cells to be fixed, stored or analyzed are the same as those described above. The composition of the cell preservative solution is the same as that described above. The present invention also includes a cell preservative solution essentially consisting of a lower alcohol having 1 to 6 carbon atoms and a divalent metal ion in an aqueous solvent. The composition of the solution is described above. The present invention also includes a cell suspension liquid, comprising: a lower alcohol having 1 to 6 carbon atoms; a divalent metal ion and fixed cells in an aqueous solvent. The cell suspension liquid can be prepared by mixing the cell preservative solution stated above and cells. The cells are fixed by the cell preservative solution.

Hereinafter, the present invention will be described in detail with reference to examples, however the present invention is not limited to the examples.

EXAMPLES

Example 1

Cells were stored in the cell preservative solution of the embodiment and then the storage stability of DNA in the cells was examined. For comparison, the same examination was performed using a commercially available cell preservative solution.
1. Materials
(1-1) Cell Preservative Solution A cell preservative solution was prepared by mixing methanol (Wako Pure Chemical Industries, Ltd.) and magnesium chloride (Kishida Chemical Co., Ltd.) so as to have the composition shown in Table 1 below (hereinafter, also referred to as "cell preservative solution of Example 1"). In preparation of the cell preservative solution, water was used as a solvent and PIPES (DOJINDO LABORATORIES) as a buffer was added so as to give a concentration of 20 mM. A NaOH aqueous solution was used to adjust the pH. The cell preservative solution had a pH of 6.7. As the commercially available cell preservative solution, PreservCyt (registered trademark) (Hologic, Inc.) was used. Although the detailed composition of PreservCyt (registered trademark) is not publicly available, it is known to be an aqueous buffer containing methanol as a main component. According to the composition analysis using the ICP emission spectrophotometer (SII Nanotechnology Inc.), divalent metal ions were not detected in PreservCyt (registered trademark).

TABLE 1

| Cell preservative solution of Example 1 | |
|---|---|
| Methanol | 43 v/v % |
| $MgCl_2$ | 20 mmol/L |

(1-2) Cells

As cells to be stored in the cell preservative solution, human cervical cancer cell lines HeLa (purchased from American Type Culture Collection (ATCC)) were used. HeLa cells were cultured in Dulbecco's modified Eagle's medium (DMEM: Sigma-Aldrich Co. LLC.) containing 10% fetal bovine serum (FBS: HyClone Laboratories, Inc.) at 37° C. in a 5% $CO_2$ atmosphere.
2. Examination of Storage Stability of DNA
(2-1) Storage of Cells Cultured HeLa cells were collected by an ordinary method and calculated. HeLa cells ($1\times10^6$ cells) were added to 12 mL of the cell preservative solution of Example 1 or 12 mL of a commercially available cell preservative solution which had been dispensed into a 15 mL volume plastic tube (Labcon), thereby immersing the cells in the cell preservative solution. These cells were stored under the temperature condition of 1° C. or 31° C. for 2 weeks, 1 month, or 2 months. It should be noted that, in clinical practice, cells are generally stored in a refrigerator (at about 4° C.). A temperature of "1° C." (i.e., the temperature condition set in this example) is lower than that of the refrigerator. In this example, the experiment was also performed at a temperature higher than room temperature (31° C.) in order to examine whether the cell preservative solution could be used at room temperature in clinical practice.

(2-2) DNA Extraction

A sample containing HeLa cells and a preservative solution was centrifuged at 10,000 rpm for 1 minute and the supernatant was removed. DNA was extracted from collected cells using the QIAamp DNA Mini Kit (manufactured by QIAGEN). The specific operation was carried out according to the manual attached to the kit. As control, DNA was extracted in the same manner as described above from HeLa cells which had been immersed in the cell preservative solution of Example 1 or the commercially available cell preservative solution for 3 hours (hereinafter, also referred to as "cells immediately after fixation").

(2-3) Electrophoresis

The absorbance of each of the DNA solutions was measured using a spectrophotometer (Nanodrop2000, manufactured by Thermo Fisher Scientific) and DNA concentrations were obtained. Samples for agarose gel electrophoresis were prepared from the DNA solutions so that the amount of DNA contained in each of the samples was 500 ng/lane. The resulting samples were subjected to 0.5% agarose gel electrophoresis.

3. Results

FIG. 1 shows the results of electrophoresis. As shown in FIG. 1, when the commercially available cell preservative solution was used, the length of a nucleotide sequence in the DNA obtained from the cells stored for a certain period was shorter than that in the DNA obtained from the cells immediately after fixation. This indicates that the DNA was degraded. This shows that, in the case of the commercially available cell preservative solution, the DNA was not appropriately maintained during storage. Therefore, it is suggested that, in the case of using the commercially available cell preservative solution, the DNA analysis of the stored cells may not be appropriately carried out. Meanwhile, when the cell preservative solution of Example 1 was used, the length of a nucleotide sequence in the DNA obtained from the cells stored under any temperature conditions during any storage periods was almost the same as the length of a nucleotide sequence in the DNA obtained from the cells immediately after fixation. Accordingly, it was suggested that when the cell preservative solution of Example 1 is used, DNA analysis can be appropriately performed even after storage of the cells for a certain period.

Example 2

The storage stability of DNA in cells was examined by storing cells in the cell preservative solution of Example 1 and then detecting a predetermined nucleic acid in DNA of the cells (HPV-derived nucleic acid). For comparison, PreservCyt (registered trademark, Hologic, Inc.), i.e., the commercially available cell preservative solution, was used to perform the same examination.

1. Examination of Storage Stability of DNA in Commercially Available Cell Preservative Solution (1-1) Storage of Cells Cervical cells (eight specimens) were extracted from the uterine cervix of eight subjects. The eight specimens were respectively added to 12 mL of PreservCyt (registered trademark) and the cells were immersed in the cell preservative solution. The specimens were divided into three equal parts to obtain aliquots 1 to 3. The aliquot 1 was subjected to nucleic acid detection described later, immediately after addition to the cell preservative solution (immediately after fixation). The aliquot 2 was subjected to nucleic acid detection described later after storage at 1° C. for 1 month or 2 months. The aliquot 3 was subjected to nucleic acid detection described later after storage at 31° C. for 1 month or 2 months. The specimen number of each of the specimens and storage conditions are shown in Table 2.

TABLE 2

| Specimen | Storage conditions | | |
|---|---|---|---|
| number | Aliquot 1 | Aliquot 2 | Aliquot 3 |
| A4015 | 0 day (immediately after fixation) | at 1° C. for 2 months | at 31° C. for 2 months |
| A4016 | 0 day (immediately after fixation) | at 1° C. for 2 months | at 31° C. for 2 months |
| A4017 | 0 day (immediately after fixation) | at 1° C. for 1 month | at 31° C. for 1 month |
| A4019 | 0 day (immediately after fixation) | at 1° C. for 2 months | at 31° C. for 2 months |
| A4020 | 0 day (immediately after fixation) | at 1° C. for 1 month | at 31° C. for 1 month |
| A4038 | 0 day (immediately after fixation) | at 1° C. for 2 months | at 31° C. for 2 months |
| A4039 | 0 day (immediately after fixation) | at 1° C. for 2 months | at 31° C. for 2 months |
| A4040 | 0 day (immediately after fixation) | at 1° C. for 2 months | at 31° C. for 2 months |

(1-2) Detection of Nucleic Acid

In Example 2, the nucleic acid derived from HPV which infected cervical cells was detected by the hybrid capture (HC) method. As the pretreatment of the HC method, DNA of the cells contained in each of the aliquots was extracted using the HC2 Sample Conversion Kit (Product No. 5127-1220, QIAGEN). The specific operation was carried out according to the manual attached to the kit. The HPV-DNA detection kit (HPV DNA "QIAGEN" HCII (Product No. 618915, QIAGEN)) was used to detect the HPV-derived nucleic acid in the DNA obtained from each of the aliquots. The specific operation was carried out according to the manual attached to the kit.

(1-3) Results

Figure 2A:
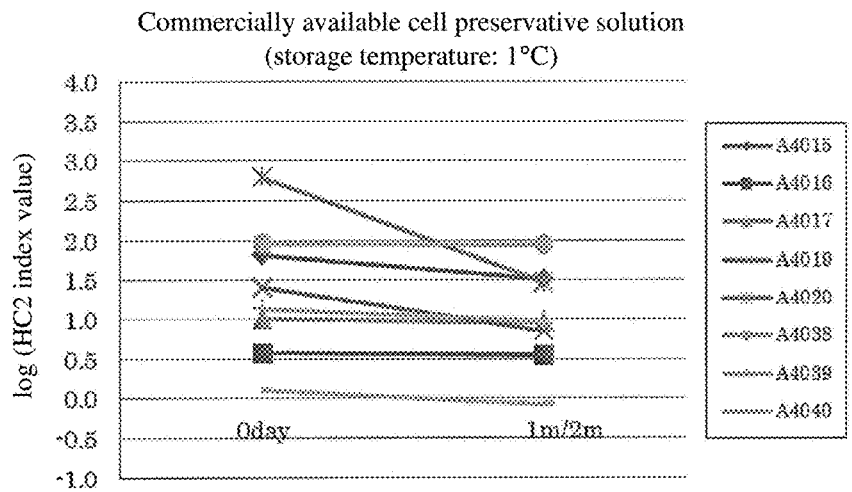
FIG. 2A is a graph showing measured values obtained by storing cervical cells extracted from subjects in the commercially available cell preservative solution under predetermined conditions and detecting human papilloma virus (HPV)-derived nucleic acids in DNA of the cells by a hybrid capture (HC) method.
Figure 2B:
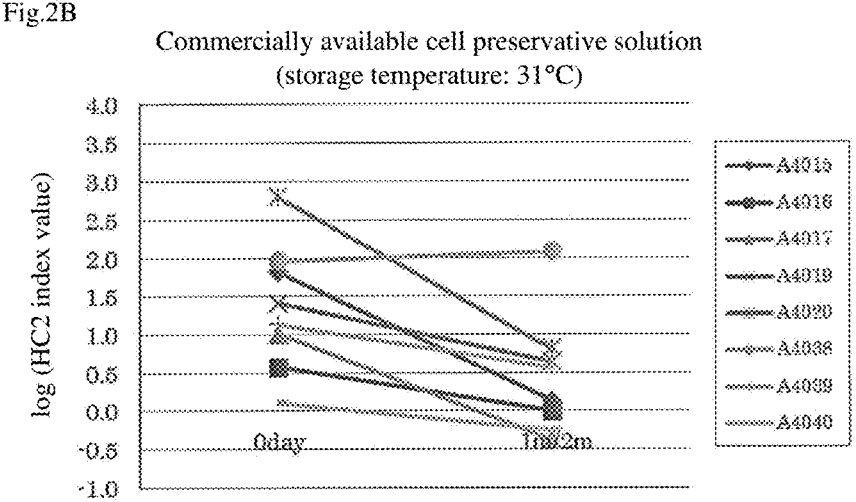
FIG. 2B is a graph showing measured values obtained by storing cervical cells extracted from subjects in the commercially available cell preservative solution under predetermined conditions and detecting HPV-derived nucleic acids in DNA of the cells by the HC method.

The results are shown in FIGS. 2A and 2B. In the figures, a vertical axis indicates a logarithm of the chemiluminescence intensity measured by the HC method (HC2 index value), "0 day" on a horizontal axis indicates that the storage period is zero day (immediately after fixation), and "1 m/2 m" indicates that the storage period is 1 month or 2 months. As shown in FIG. 2A, the HC2 index value of the aliquot 2 tended to be decreased compared to the HC2 index value of the aliquot 1. As shown in FIG. 2B, the HC2 index value of the aliquot 3 was decreased compared to the HC2 index value of the aliquot 1. These results reveal that the cervical cells extracted from the subjects were stored in the commercially available cell preservative solution at 1° C. or 31° C. for 1 month or for 2 months, so that the nucleic acids in the cells were degraded.

2. Examination of Storage Stability of DNA in Cell Preservative Solution of Embodiment (2-1) Storage of Cells Cervical cells (twelve specimens) were extracted from the uterine cervix of twelve subjects who were different from the eight subjects. The twelve specimens were respectively added to 12 mL of the cell preservative solution of Example 1 and thus the cells were immersed in the cell preservative solution. The specimens were divided into three equal parts to obtain aliquots 1 to 3. The cells were collected from the aliquot 1, immediately after addition to the cell preservative solution (immediately after fixation) and the collected cells were stored at −60° C. 2 months later, nucleic acid detection described later was performed on the cells collected from the aliquot 1 as well as the cells from the aliquots 2 and 3. The aliquot 2 was subjected to nucleic acid detection described later after storage at 1° C. for 2 months. The aliquot 3 was subjected to nucleic acid detection described later after storage at 31° C. for 2 months. The specimen number of each of the specimens and storage conditions are shown in

TABLE 3

| Specimen number | Storage conditions | | |
|---|---|---|---|
| | Aliquot 1 | Aliquot 2 | Aliquot 3 |
| A4339 | 0 day (immediately after fixation) | at 1° C. for 2 months | at 31° C. for 2 months |
| A4340 | 0 day (immediately after fixation) | at 1° C. for 2 months | at 31° C. for 2 months |
| A4343 | 0 day (immediately after fixation) | at 1° C. for 2 months | at 31° C. for 2 months |
| A4351 | 0 day (immediately after fixation) | at 1° C. for 2 months | at 31° C. for 2 months |
| A4352 | 0 day (immediately after fixation) | at 1° C. for 2 months | at 31° C. for 2 months |
| A4365 | 0 day (immediately after fixation) | at 1° C. for 2 months | at 31° C. for 2 months |
| A4366 | 0 day (immediately after fixation) | at 1° C. for 2 months | at 31° C. for 2 months |
| H-0072 | 0 day (immediately after fixation) | at 1° C. for 2 months | at 31° C. for 2 months |
| H-0073 | 0 day (immediately after fixation) | at 1° C. for 2 months | at 31° C. for 2 months |
| C-0113 | 0 day (immediately after fixation) | at 1° C. for 2 months | at 31° C. for 2 months |
| C-0127 | 0 day (immediately after fixation) | at 1° C. for 2 months | at 31° C. for 2 months |
| C-0131 | 0 day (immediately after fixation) | at 1° C. for 2 months | at 31° C. for 2 months |

(2-2) Detection of Nucleic Acid

In the same manner as described above, the nucleic acid derived HPV which infected cervical cells was detected by the hybrid capture (HC) method. The pretreatment of the HC method and the detection of the nucleic acid by the HC method were performed using the HC2 Sample Conversion Kit (QIAGEN) and the HPV DNA "QIAGEN" HCII (QIAGEN), respectively. The specific operation was carried out according to the manual attached to each kit.

(2-3) Results

Figure 3A:
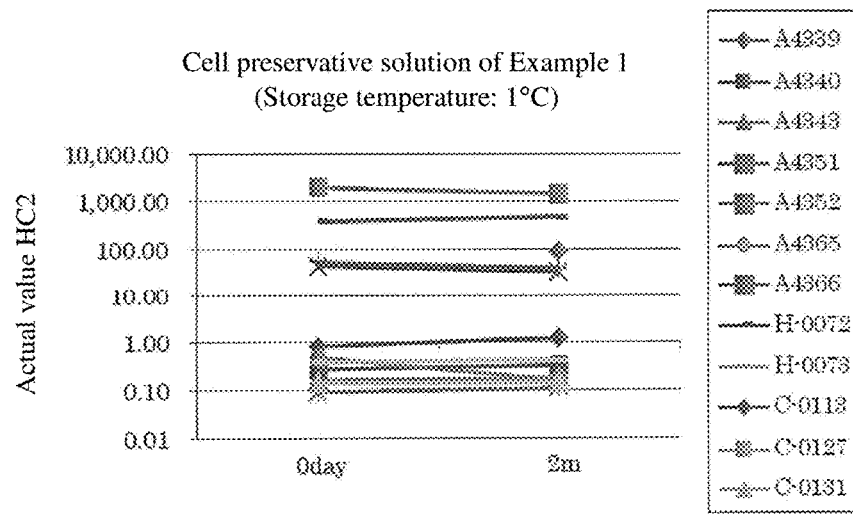
FIG. 3A is a graph showing measured values obtained by storing cervical cells extracted from subjects in the cell preservative solution of the embodiment under predetermined conditions and detecting HPV-derived nucleic acids in DNA of the cells by the HC method.
Figure 3B:
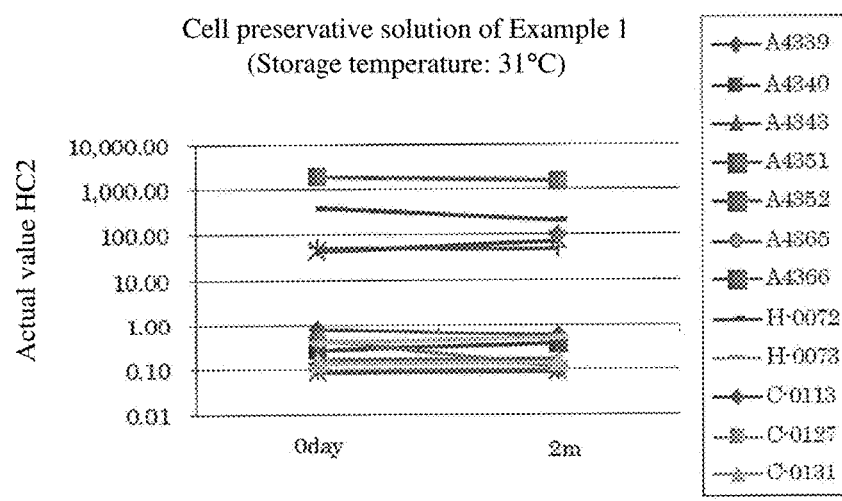
FIG. 3B is a graph showing measured values obtained by storing cervical cells extracted from subjects in the cell preservative solution of the embodiment under predetermined conditions and detecting HPV-derived nucleic acids in DNA of the cells by the HC method.

The results are shown in FIGS. 3A and 3B. In the figures, a vertical axis indicates the chemiluminescence intensity measured by the HC method (HC2 index value), "0 day" on a horizontal axis indicates that the storage period is zero day (immediately after fixation), and "2 m" indicates that the storage period is 2 months. As shown in FIG. 3A, the HC2 index value of the aliquot 2 was almost equivalent to the HC2 index value of the aliquot 1. As shown in FIG. 3B, the HC2 index value of the aliquot 3 was almost equivalent to the HC2 index value of the aliquot 1. These results reveal that even if the cervical cells extracted from the subjects were stored in the cell preservative solution of Example 1 at 1° C. or 31° C. for 2 months, the nucleic acids in the cells could be appropriately maintained.

Example 3

It was examined whether cells stored in the cell preservative solution of Example 1 were suitable for staining cellular specimens. For comparison, cells stored in PreservCyt (registered trademark, Hologic, Inc.), i.e., the commercially available cell preservative solution, was used.

1. Staining of Cells Stored in Commercially Available Cell Preservative Solution Cells extracted from the uterine cervix of subjects were suspended in 20 mL of PreservCyt (registered trademark) and allowed to stand at room temperature for 2 days. The slide preparation system ThinPrep2000 (Hologic, Inc.) was used to produce a slide with the cells from the cell suspension adhered thereto. The specific operation was carried out according to the operation manual of the apparatus. The produced slide was stained with Papanicolaou stain in accordance with the procedure shown in Table 4 below.

TABLE 4

| Procedure | Staining tank | Time |
|---|---|---|
| 1 | 70% ethanol | 2 min |
| 2 | 50% ethanol | 2 min |
| 3 | Rinsed with water | 2 min |
| 4 | 1.5-fold dilution, Gill's Hematoxylin | 4 min |
| 5 | Rinsed with running water | 5 min |
| 6 | 0.2% hydrochloric acid alcohol | 1 min |
| 7 | Rinsed with running water | 2 min |
| 8 | 70% ethanol | 2 min |
| 9 | 95% ethanol | 2 min × 4 tanks |
| 10 | OG6 (Orange G6) | 2 min |
| 11 | 95% ethanol | 2 min × 4 tanks |
| 12 | EA (Eosin) | 2 min |
| 13 | 100% ethanol | 2 min × 4 tanks |
| 14 | Xylene | 5 min × 4 tanks |

2. Staining of Cells Stored in Cell Preservative Solution of Embodiment

Cells extracted from the uterine cervix of subjects were suspended in 20 mL of the cell preservative solution of Example 1 and allowed to stand at room temperature for 2 days. Then, the cell suspension was centrifuged at 800 g for 10 minutes and the supernatant was removed. 200 μL of deionized water was added to the precipitate so as to give a suspension. Then, the total amount of the resulting suspension was added to the chamber (BD Settling Chamber, Becton, Dickinson and Company) installed in the slide glass (BD SurePath PreCoat Slide, Becton, Dickinson and Company) and allowed to stand for 10 minutes. Thereafter, the cells on the slide were fixed with 95% ethanol. The produced slide was stained with Papanicolaou stain in accordance with the procedure shown in Table 4 above.

3. Results

Figure 4:
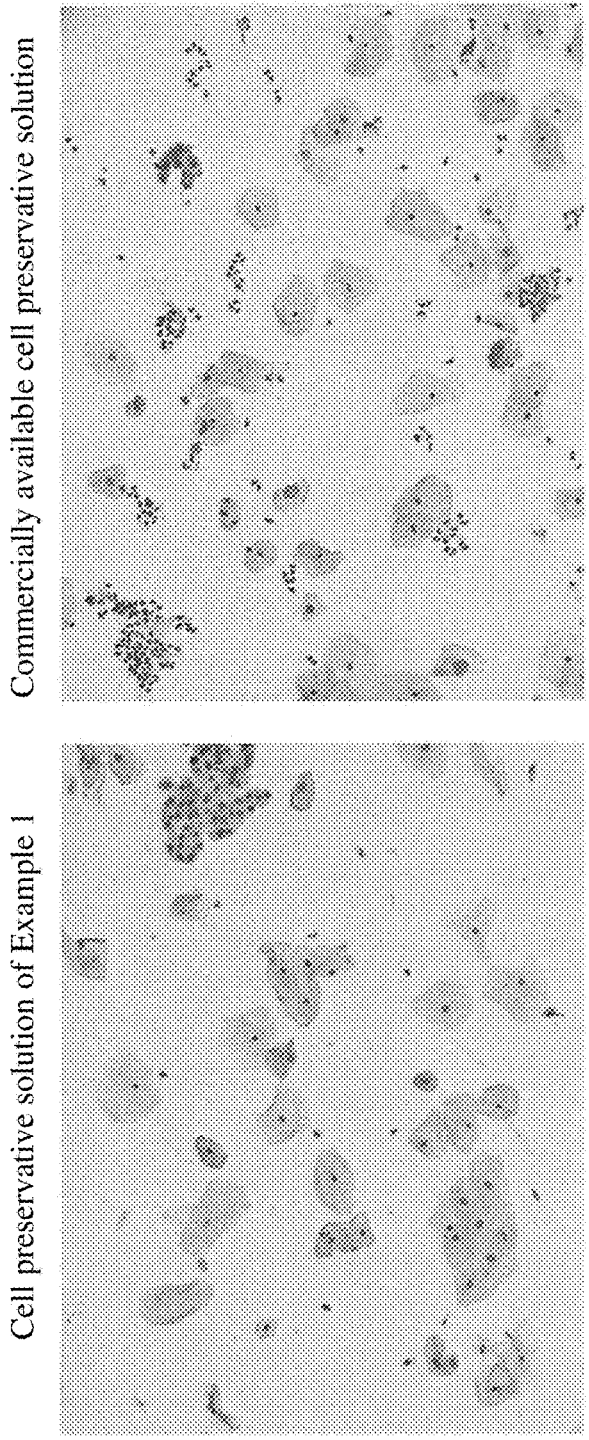
FIG. 4 is a photograph taken when cervical cells extracted from subjects were stored in the cell preservative solution of the embodiment or the commercially available cell preservative solution for 2 days at room temperature and subjected to Papanicolaou staining.

The results are shown in FIG. 4. As shown in FIG. 4, the cells stored in the cell preservative solution of the embodiment was stained with Papanicolaou stain, thereby obtaining a stained image equivalent to that of the cells stored in the commercially available cell preservative solution.

Example 4

A relationship between the magnesium ion concentration in the cell preservative solution and the stability of DNA in cells was examined by flow cytometry.

1. Materials (1-1) Cell Preservative Solution

In Example 4, cell preservative solutions were prepared by mixing methanol (Wako Pure Chemical Industries, Ltd.) and magnesium chloride (Kishida Chemical Co., Ltd.) so as to have the composition shown in Table 5 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Every cell preservative solution had a pH of 6.6.

TABLE 5

|  | Methanol (v/v%) | MgCl$_2$ (mmol/L) |
|---|---|---|
| Cell preservative solution 1 | 43 | 0 |
| Cell preservative solution 2 | 43 | 1.0 |
| Cell preservative solution 3 | 43 | 2.0 |
| Cell preservative solution 4 | 43 | 20 |

(1-2) Cells

As cells stored in the cell preservative solution, human cervical cancer cell lines HeLa (purchased from ATCC) were used. The HeLa cells were cultured in the same manner as in Example 1.

(1-3) Reagent and Flow Cytometer

The GC-SEARCH KIT (SYSMEX CORPORATION) was used as a stain solution or an RNA remover. The GC-PACK (SYSMEX CORPORATION) was used as a diluent. The exfoliative cell analyzer: LC-1000 (SYSMEX CORPORATION) was used as a flow cytometer.

2. Storage of Cells and Flow Cytometry (FCM) Analysis

HeLa cells were added to and suspended in the cell preservative solutions 1 to 4, respectively. The resulting cell suspensions were allowed to stand at 1° C. or 31° C. for 24 hours. Each of the cell suspensions was centrifuged at 10,000 rpm for 1 minute and the supernatant was removed. To 30 μL of the remaining solution containing the cells, 1 mL of a diluent was added. The resulting mixture was centrifuged at 10,000 rpm for 1 minute and the supernatant was removed. The stain solution, RNA remover, and diluent were added to 30 μL of the remaining solution containing the cells to prepare a measurement sample. The resulting measurement sample was introduced into the flow cytometer and optical signals (a fluorescent signal and a forward scattered light signal) were obtained. Then, frequency distributions (histograms) were created, where the fluorescence area detected from each of the cells was plotted on a horizontal axis and the number of cells was plotted on a vertical axis. It should be noted that the fluorescence area is an indicator reflecting the amount of DNA in cells.

3. Results

Figure 5:
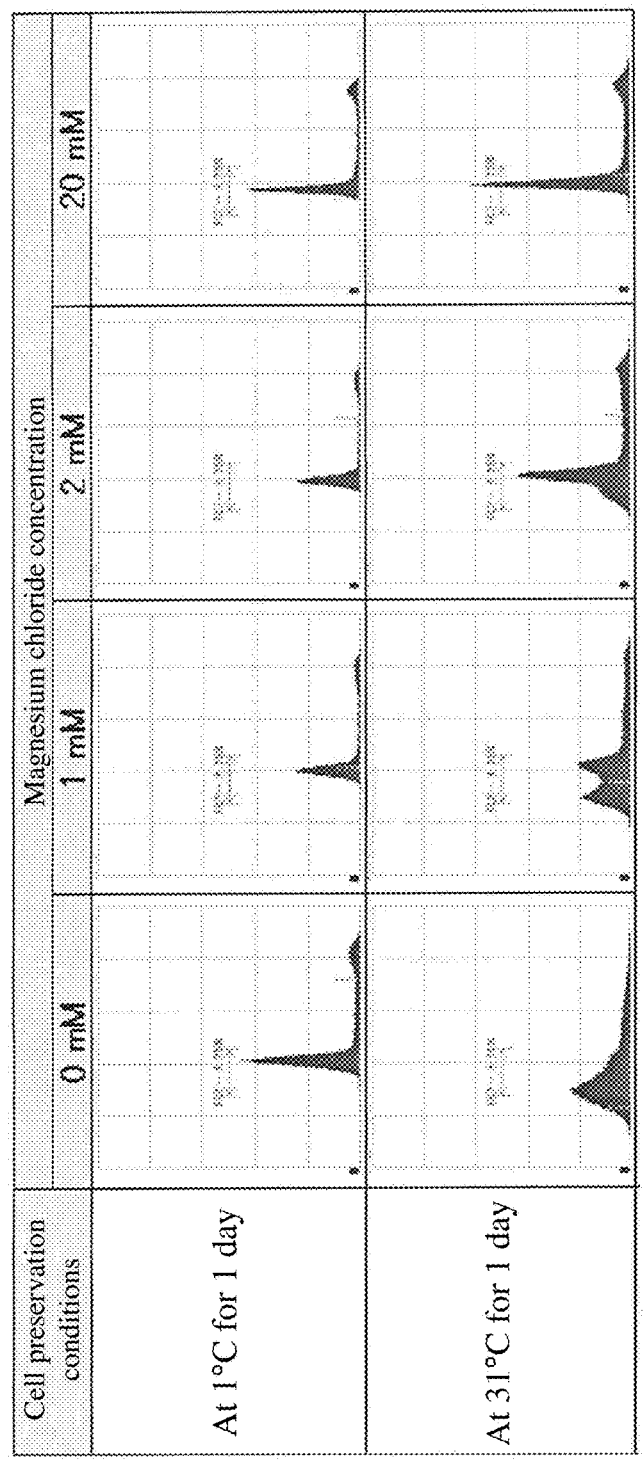
FIG. 5 shows fluorescence area histograms obtained by analyzing HeLa cells stored in cell preservative solutions having various magnesium ion concentrations under predetermined conditions with a flow cytometer.

FIG. 5 shows the created fluorescence area histograms. Here, the fluorescence area histograms will be described. It is known that two peaks are usually observed in the fluorescence area histograms. Specifically, the peaks include a peak formed from the population of diploid cells and a peak formed from the population of cells grown into tetraploid cells. The amount of DNA in the cells grown into tetraploid cells is higher than that in the diploid cells. Generally, it is known that the amount of DNA in the diploid cells is constant. Therefore, when the DNA is stable, the fluorescence areas in the diploid cells become constant, and thus a peak of the diploid cells sharply appears in the fluorescence area histograms. Meanwhile, the fluorescence area is an indicator reflecting the amount of DNA. Thus, when DNA destabilization results in its degradation or fragmentation, the amount of DNA in the diploid cells becomes less constant, thereby causing a change in the fluorescence area. As a result, the peak of the diploid cells in the histograms becomes less sharp.

As shown in FIG. 5, even if the cells were stored in any of the cell preservative solutions 1 to 4 under the temperature condition of 1° C., the histogram shapes of the fluorescence areas were normal. However, when cells were stored in the cell preservative solutions 1, 2, and 3 having a low divalent metal ion concentration at 31° C., the histogram shapes were broken. Meanwhile, when the cell preservative solution 4 having a divalent metal ion concentration of 20 mmol/L was used, no broken histogram shape was confirmed even under the temperature condition of 31° C. Accordingly, it is shown that the divalent metal ion concentration is appropriately set, whereby DNA is stably maintained even when stored at a high temperature, similarly to when stored at a low temperature, and thus it is possible to prevent the histograms from being broken.

Example 5

A relationship between the magnesium ion concentration in the cell preservative solution and the stability of DNA in cells was examined by flow cytometry.

1. Materials

In Example 5, cell preservative solutions were prepared by mixing methanol (Wako Pure Chemical Industries, Ltd.) and magnesium chloride (Kishida Chemical Co., Ltd.) so as to have the composition shown in Table 6 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.6. The cells, reagent, and flow cytometer are the same as those used in Example 4.

TABLE 6

|  | Methanol (v/v%) | MgCl$_2$ (mmol/L) |
|---|---|---|
| Cell preservative solution 5 | 43 | 0 |
| Cell preservative solution 6 | 43 | 1.0 |
| Cell preservative solution 7 | 43 | 2.0 |
| Cell preservative solution 8 | 43 | 3.0 |
| Cell preservative solution 9 | 43 | 4.0 |
| Cell preservative solution 10 | 43 | 5.0 |
| Cell preservative solution 11 | 43 | 6.0 |
| Cell preservative solution 12 | 43 | 8.0 |
| Cell preservative solution 13 | 43 | 10 |
| Cell preservative solution 14 | 43 | 20 |
| Cell preservative solution 15 | 43 | 30 |
| Cell preservative solution 16 | 43 | 40 |
| Cell preservative solution 17 | 43 | 60 |
| Cell preservative solution 18 | 43 | 80 |
| Cell preservative solution 19 | 43 | 82 |
| Cell preservative solution 20 | 43 | 85 |
| Cell preservative solution 21 | 43 | 90 |
| Cell preservative solution 22 | 43 | 92 |
| Cell preservative solution 23 | 43 | 95 |
| Cell preservative solution 24 | 43 | 100 |
| Cell preservative solution 25 | 43 | 120 |
| Cell preservative solution 26 | 43 | 200 |

2. Storage of Cells and FCM Analysis

Figure 6:
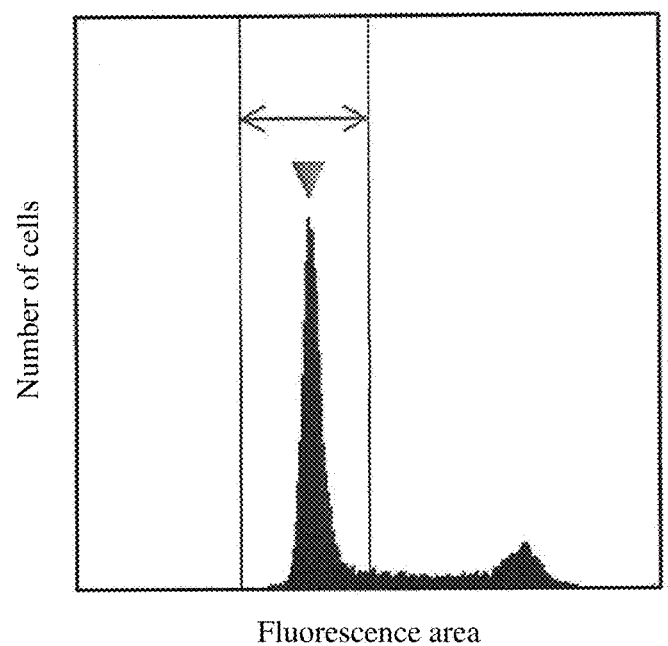
FIG. 6 is a diagram showing a diploid cell appearing region in a fluorescence area histogram obtained by analyzing HeLa cells stored in the cell preservative solution of the embodiment at 25° C. for 4 hours with the flow cytometer.

HeLa cells were added to and suspended in the cell preservative solutions 5 to 26, respectively. The resulting cell suspensions were allowed to stand at 25° C. for 4 hours or at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4. An indicator of the stability of the histogram shape was calculated as follows. It should be noted that the calculation will be described with reference to FIG. 6. On the basis of the histogram of the cells stored in the cell preservative solution 14 (with a MgCl$_2$ concentration of 20 mmol/L) at 25° C. for 4 hours, the mode in the fluorescence area in the diploid cell region was calculated. The mode corresponds to the peak as indicated by an arrowhead in FIG. 6. The diploid cell appearing region was defined as follows: the mode in the fluorescence area in the diploid cell region has a lower limit of 75% and the mode in the fluorescence area in the diploid cell region has an upper limit of 125%. In FIG. 6, this region corresponds to the region sandwiched between two lines. The coefficient of variation (CV) of the fluorescence area in the diploid cell appearing region was calculated, and this was used as an indicator of the stability of histogram shape. A larger coefficient of variation (CV) of the fluorescence area in the region indicates that the histogram shape in the diploid cells is broken.

3. Results

Figure 7A:
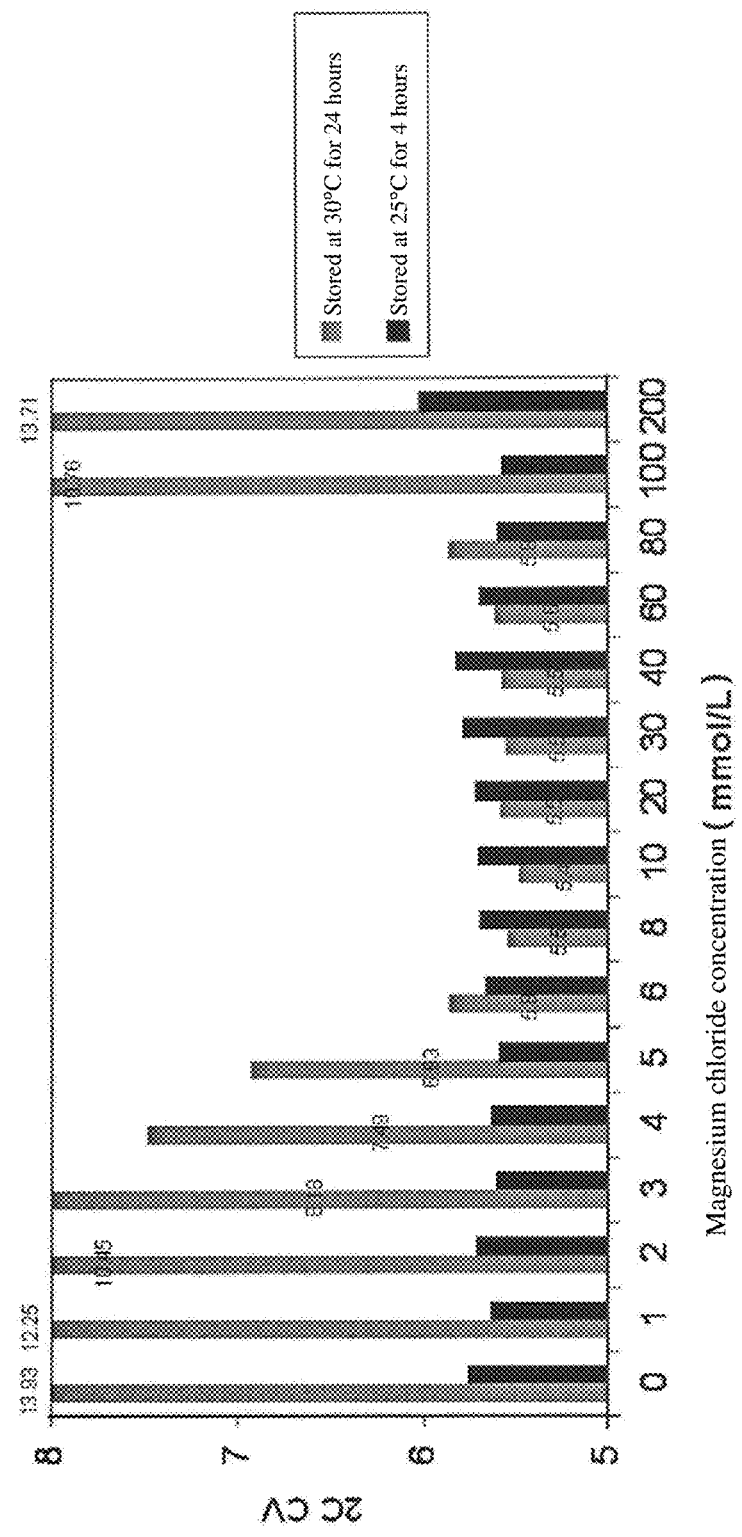
FIG. 7A is a graph showing coefficients of variation (CV) of the fluorescence area in a diploid cell appearing region as for HeLa cells stored in cell preservative solutions having various magnesium ion concentrations at 25° C. for 4 hours or at 30° C. for 24 hours.
Figure 7B:
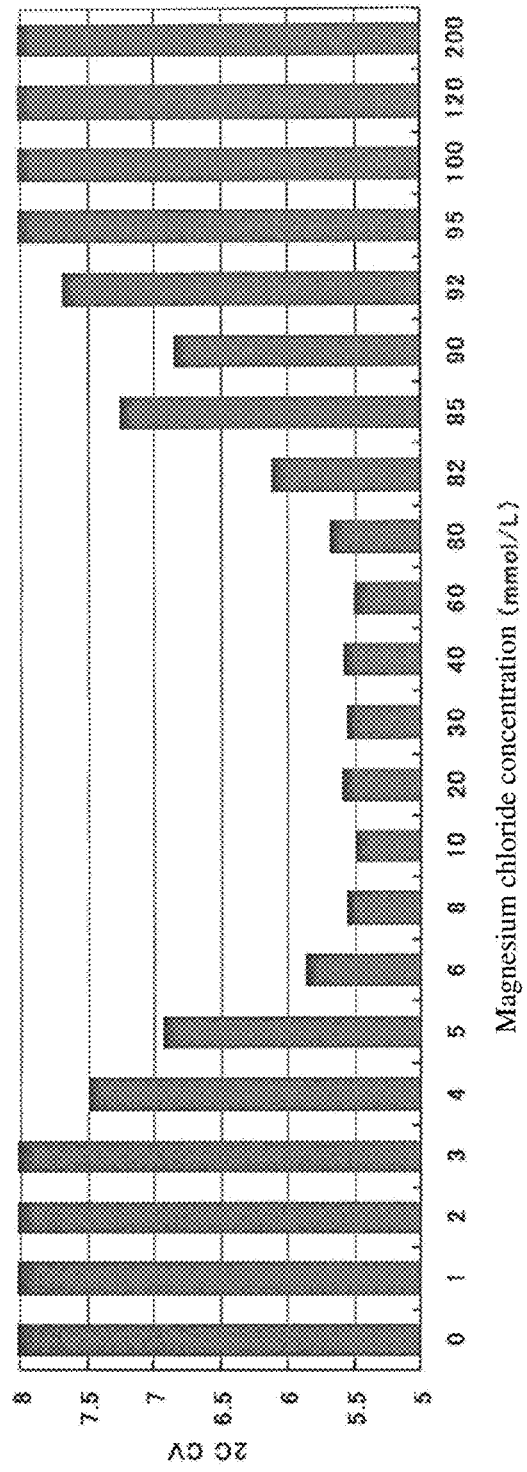
FIG. 7B is a graph showing coefficients of variation (CV) of the fluorescence area in a diploid cell appearing region as for HeLa cells stored in cell preservative solutions having various magnesium ion concentrations at 30° C. for 24 hours.

The results are shown in FIGS. 7A and 7B. As shown in FIG. 7A, in the case of storage at 25° C. for 4 hours, even if any of the cell preservative solutions having magnesium chloride concentrations in the range of 0 mmol/L to 200 mmol/L was used, the CV value in the diploid cell appearing region was low. Further, a change in the CV value due to magnesium chloride concentrations was hardly observed. Meanwhile, as shown in FIGS. 7A and 7B, in the case of storage at 30° C. for 24 hours, the CV value in the diploid cell appearing region was significantly increased when using the cell preservative solution having a high or low concentration of magnesium chloride. From these results, it was confirmed that when the cell preservative solutions 11 to 19 were used, namely when the divalent metal ion concentration in the cell preservative solution was from 6 mmol/L to 82 mmol/L, there was an effect of preventing the histogram shape from being broken. As described above, the fluorescence area is an indicator reflecting the amount of DNA in cells. Thus, when DNA destabilization results in its degradation or fragmentation, the amount of DNA in the diploid cells becomes less constant, thereby causing a change in the fluorescence area. As a result, the histogram shape in the diploid cells is broken. Therefore, it is assumed that setting of the divalent metal ion concentration in the cell preservative solution to a range of from 6 mmol/L to 82 mmol/L contributed to stabilization of DNA in cells.

Example 6

A relationship between the lower alcohol concentration of the cell preservative solution and the stability of DNA in cells was examined by flow cytometry.

1. Materials

In Example 6, cell preservative solutions were prepared by mixing methanol (Wako Pure Chemical Industries, Ltd.) and magnesium chloride (Kishida Chemical Co., Ltd.) so as to have the composition shown in Table 7 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.7. The cells, reagent, and flow cytometer are the same as those used in Example 4.

TABLE 7

|  | Methanol (v/v%) | MgCl$_2$ (mmol/L) |
| --- | --- | --- |
| Cell preservative solution 27 | 40 | 10 |
| Cell preservative solution 28 | 40 | 20 |
| Cell preservative solution 29 | 40 | 40 |
| Cell preservative solution 30 | 45 | 10 |
| Cell preservative solution 31 | 45 | 20 |
| Cell preservative solution 32 | 45 | 40 |
| Cell preservative solution 33 | 38 | 10 |
| Cell preservative solution 34 | 38 | 20 |
| Cell preservative solution 35 | 38 | 40 |
| Cell preservative solution 36 | 38 | 60 |
| Cell preservative solution 37 | 48 | 10 |
| Cell preservative solution 38 | 48 | 20 |
| Cell preservative solution 39 | 48 | 40 |
| Cell preservative solution 40 | 48 | 60 |
| Cell preservative solution 41 | 35 | 20 |
| Cell preservative solution 42 | 35 | 40 |
| Cell preservative solution 43 | 43 | 20 |
| Cell preservative solution 44 | 43 | 40 |
| Cell preservative solution 45 | 50 | 20 |
| Cell preservative solution 46 | 50 | 40 |

2. Storage of Cells and FCM Analysis

HeLa cells were added to and suspended in the cell preservative solutions 27 to 46, respectively. The resulting cell suspensions were allowed to stand at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 8A:
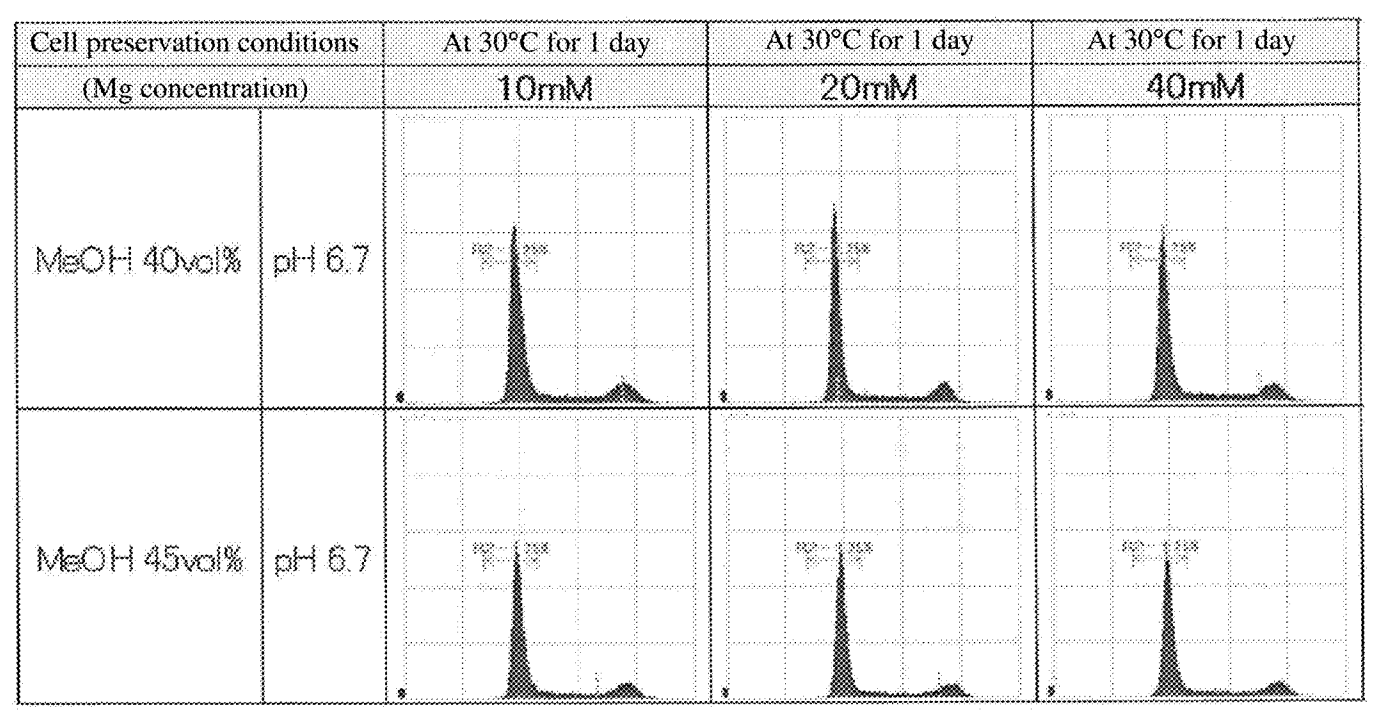
Figure 8B:
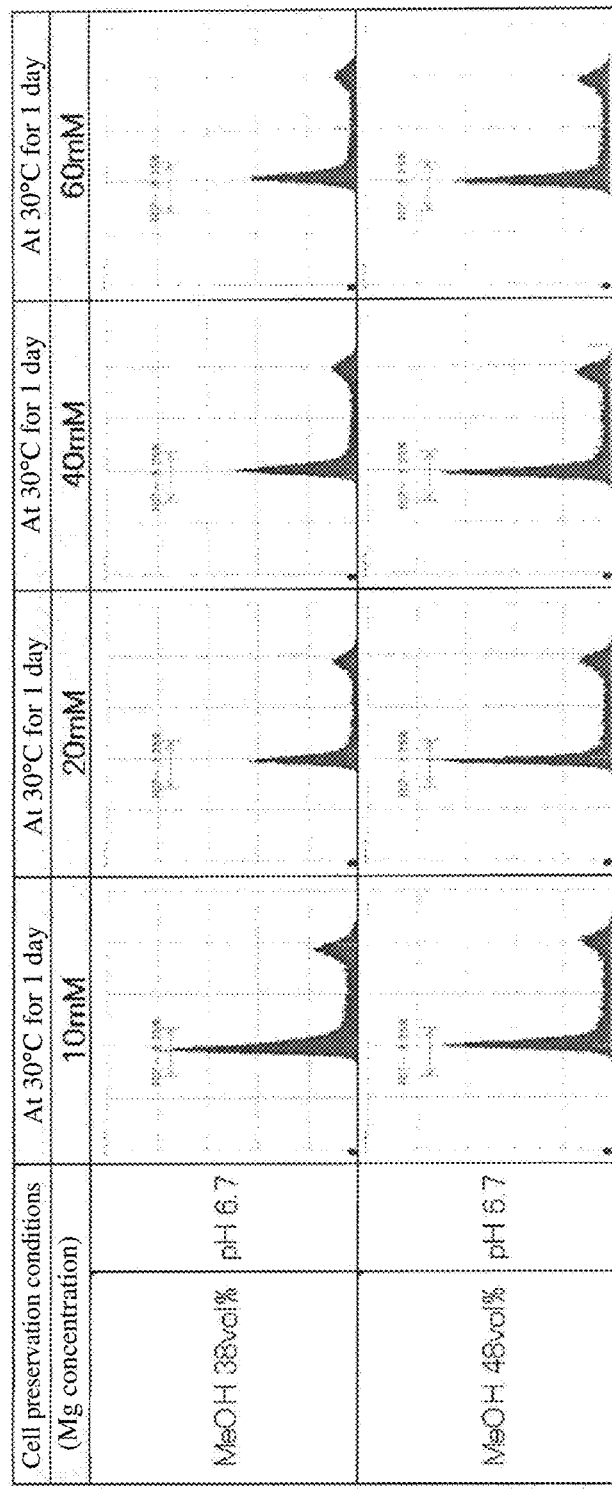
FIG. 8B shows fluorescence area histograms obtained by analyzing HeLa cells stored in cell preservative solutions having various methanol concentrations under predetermined conditions with the flow cytometer.
Figure 8C:
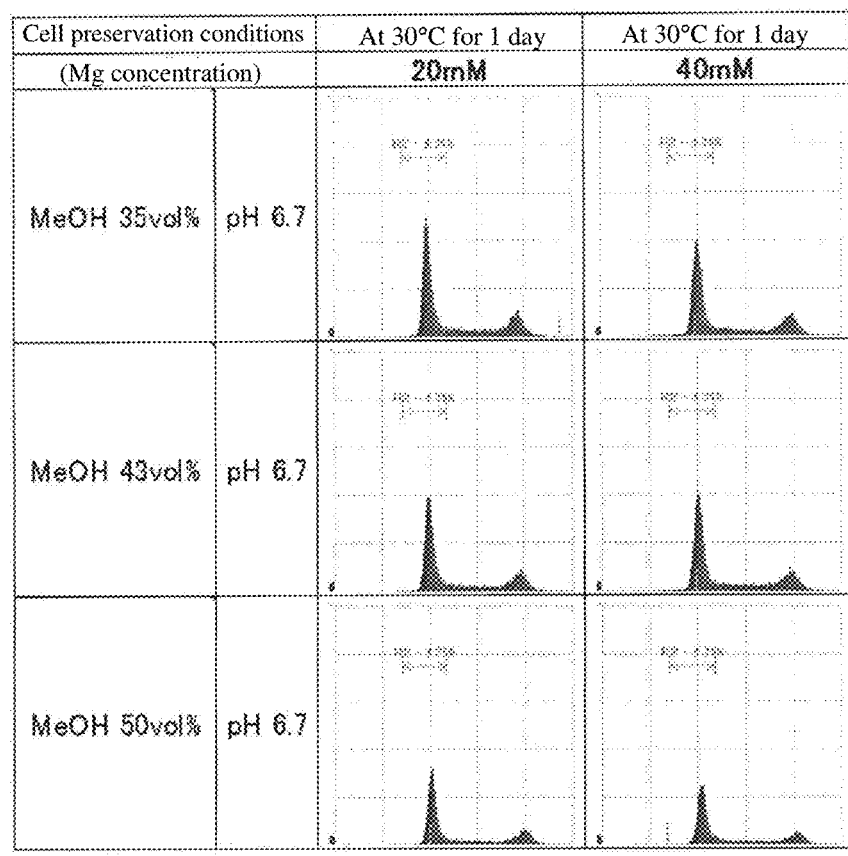
FIG. 8C shows fluorescence area histograms obtained by analyzing HeLa cells stored in cell preservative solutions having various methanol concentrations under predetermined conditions with the flow cytometer.

FIGS. 8A, 8B, and 8C show the created fluorescence area histograms. As shown in FIGS. 8A and 8B, when the divalent metal ion concentration in the cell preservative solution was from 10 mmol/L to 60 mmol/L, even if the methanol (MeOH) concentration was from 38 v/v % to 48 v/v %, the histogram shapes of the fluorescence areas were favorably maintained. As shown in FIG. 8C, when the divalent metal ion concentration in the cell preservative solution was 20 mmol/L or 40 mmol/L, even if the methanol concentration was 35 v/v % or 50 v/v %, the histogram shapes of the fluorescence areas were favorably maintained.

Example 7

A relationship between the pH of the cell preservative solution and the stability of DNA in cells was examined by flow cytometry.

1. Materials

In Example 7, cell preservative solutions were prepared by mixing methanol (Wako Pure Chemical Industries, Ltd.) and magnesium chloride (Kishida Chemical Co., Ltd.) so as to have the composition shown in Table 8 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions 47 to 50 had a pH of 6.4 and each of the cell preservative solutions 51 to 54 had a pH of 7.0. The cells, reagent, and flow cytometer are the same as those used in Example 4.

TABLE 8

|  | Methanol (v/v%) | MgCl$_2$ (mmol/L) |
|---|---|---|
| Cell preservative solution 47 | 43 | 10 |
| Cell preservative solution 48 | 43 | 20 |
| Cell preservative solution 49 | 43 | 40 |
| Cell preservative solution 50 | 43 | 60 |
| Cell preservative solution 51 | 43 | 10 |
| Cell preservative solution 52 | 43 | 20 |
| Cell preservative solution 53 | 43 | 40 |
| Cell preservative solution 54 | 43 | 60 |

2. Storage of Cells and FCM Analysis

HeLa cells were added to and suspended in the cell preservative solutions 47 to 54, respectively. The resulting cell suspensions were allowed to stand at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 9:
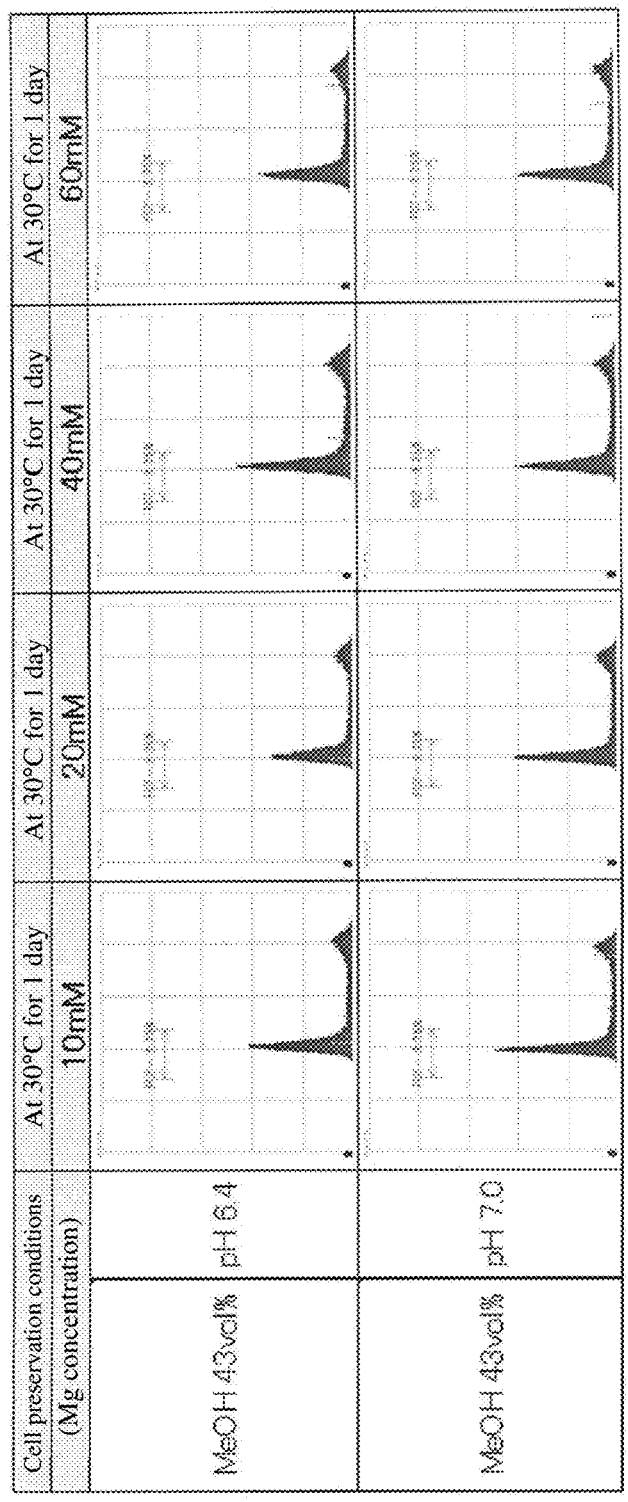
FIG. 9 shows fluorescence area histograms obtained by analyzing HeLa cells stored in a cell preservative solution with a pH of 6.4 or 7.0 under predetermined conditions with the flow cytometer.

FIG. 9 shows the created fluorescence area histograms. As shown in FIG. 9, when the divalent metal ion concentration in the cell preservative solution was from 10 mmol/L to 60 mmol/L, even if the pH was 6.4 or 7.0, the histogram shapes of the fluorescence areas were favorably maintained.

Example 8

A relationship between the calcium ion concentration in the cell preservative solution and the stability of DNA in cells was examined by flow cytometry using a calcium ion as a divalent metal ion.

1. Materials

In Example 8, cell preservative solutions were prepared by mixing methanol (Wako Pure Chemical Industries, Ltd.) and calcium chloride (Kishida Chemical Co., Ltd.) so as to have the composition shown in Table 9 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.7. The cells, reagent, and flow cytometer are the same as those used in Example 4.

TABLE 9

|  | Methanol (v/v%) | CaCl$_2$ (mmol/L) |
|---|---|---|
| Cell preservative solution 55 | 43 | 0 |
| Cell preservative solution 56 | 43 | 1.0 |
| Cell preservative solution 57 | 43 | 20 |

2. Storage of Cells and FCM Analysis

HeLa cells were added to and suspended in the cell preservative solutions 55 to 57, respectively. The resulting cell suspensions were allowed to stand at 1° C. or 31° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 10:
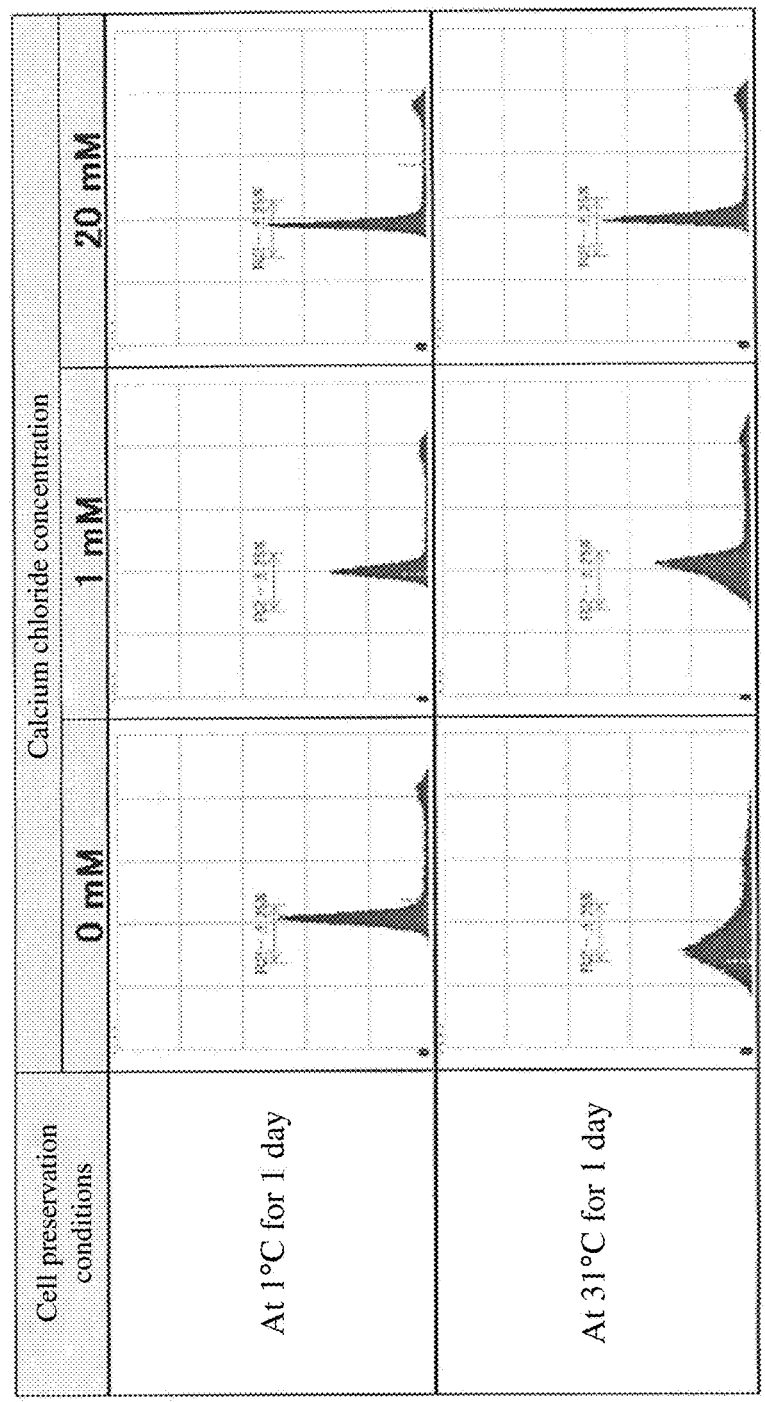
FIG. 10 shows fluorescence area histograms obtained by analyzing HeLa cells stored in cell preservative solutions having various calcium ion concentrations under predetermined conditions with the flow cytometer.

FIG. 10 shows the created fluorescence area histograms. As shown in FIG. 10, even if cells were stored in any of the cell preservative solutions 55 to 57 under the temperature condition of 1° C., the histogram shapes of the fluorescence areas were normal. However, when cells were stored in the cell preservative solutions 55 and 56 having a low divalent metal ion concentration at 31° C., the histogram shapes were broken. Meanwhile, when the cell preservative solution 57 having a divalent metal ion concentration of 20 mmol/L was used, no broken histogram shape was confirmed even if the temperature condition was 31° C. Accordingly, it was shown that, by setting the divalent metal ion concentration appropriately, DNA was stably maintained even when stored at a high temperature, similarly to when stored at a low temperature, and thus it is possible to prevent the histograms from being broken.

Comparative Example 1

As for the cells stored in the commercially available cell preservative solution, the stability of DNA was examined by flow cytometry.

1. Materials

In Comparative Example 1, PreservCyt (registered trademark, Hologic, Inc.) was used as the commercially available cell preservative solution. The cells, reagent, and flow cytometer are the same as those used in Example 4.

2. Storage of Cells and FCM Analysis

HeLa cells were added to and suspended in PreservCyt (registered trademark). The resulting cell suspension was allowed to stand at room temperature for 30 minutes, at 31° C. for 24 hours, or at 31° C. for 7 days. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 11:
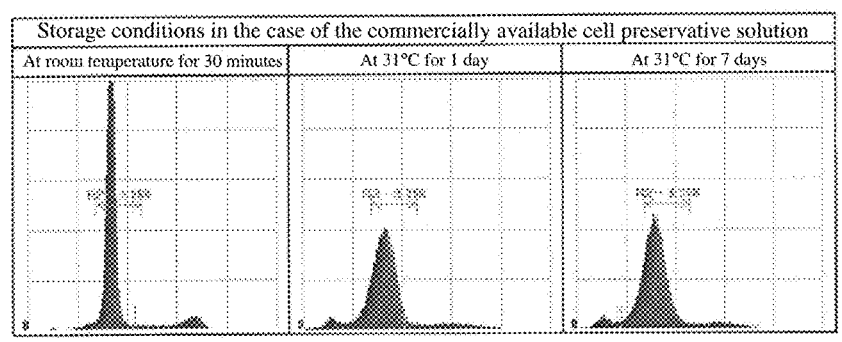
FIG. 11 is fluorescence area histograms obtained by analyzing HeLa cells stored in the commercially available cell preservative solution under predetermined conditions with the flow cytometer.

FIG. 11 shows the created fluorescence area histograms. As shown in FIG. 11, in the case of storage at room temperature for 30 minutes, the histogram shape in the fluorescence area was normal. However, in the case of storage at 31° C. for 24 hours or 7 days, the histogram shapes were broken. Therefore, it is found that the commercially available cell preservative solution is different from the cell preservative solution of the embodiment and not suitable for storage under the temperature condition of 31° C.

Example 9

A relationship between the calcium ion concentration in the cell preservative solution and the stability of DNA in cells was examined by flow cytometry.

1. Materials (1-1) Cell Preservative Solution

In Example 9, cell preservative solutions were prepared by mixing methanol (Wako Pure Chemical Industries, Ltd.) and calcium chloride (Kishida Chemical Co., Ltd.) so as to have the composition shown in Table 10 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.6. The cells, reagent, and flow cytometer are the same as those used in Example 4.

TABLE 10

|  | Methanol (v/v%) | CaCl$_2$ (mmol/L) |
|---|---|---|
| Cell preservative solution 58 | 43 | 0 |
| Cell preservative solution 59 | 43 | 1.0 |
| Cell preservative solution 60 | 43 | 6.0 |
| Cell preservative solution 61 | 43 | 20 |
| Cell preservative solution 62 | 43 | 82 |
| Cell preservative solution 63 | 43 | 100 |
| Cell preservative solution 64 | 43 | 200 |

2. Storage of Cells and FCM Analysis

HeLa cells were added to and suspended in the cell preservative solutions 58 to 64, respectively. The resulting cell suspensions were allowed to stand at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 13:
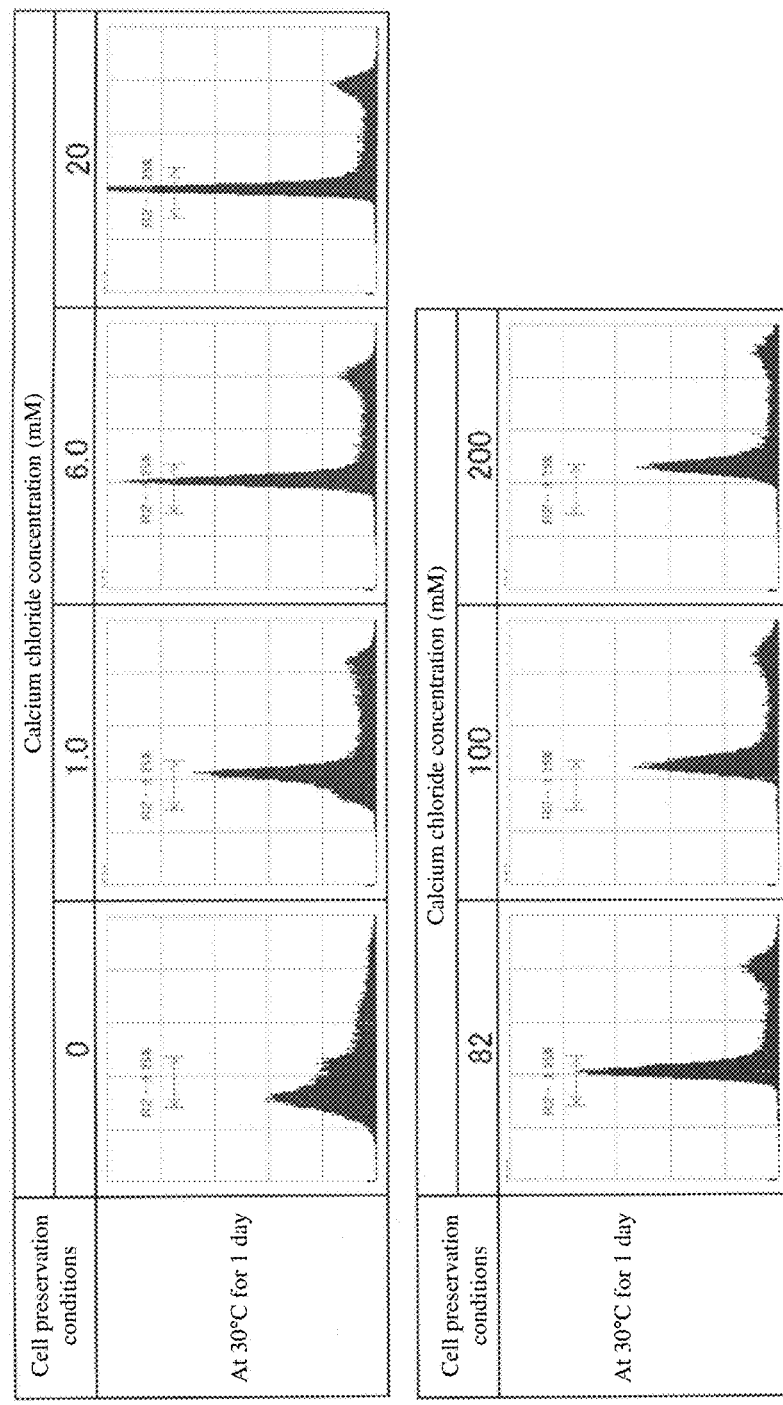
FIG. 13 shows fluorescence area histograms obtained by analyzing HeLa cells stored in cell preservative solutions having various calcium ion concentrations under predetermined conditions with the flow cytometer.

FIG. 13 shows the created fluorescence area histograms. As shown in FIG. 13, when cells were stored in the cell preservative solutions 60, 61, and 62 having calcium ion concentrations of 6, 20, and 82 mmol/L, respectively at 30° C., the histogram shapes were favorable. As described above, the fluorescence area is an indicator reflecting the amount of DNA in cells. Hence, the fact that the histogram shapes of the fluorescence areas are favorable means that DNA in cells has been stably maintained during storage. Therefore, it was shown that, by setting the calcium ion concentration suitably, DNA in cells could be stably maintained even when stored under the temperature condition of 30° C.

Example 10

Cells were fixed and stored in a cell preservative solution containing both magnesium and calcium ions as divalent metal ions. The stability of DNA in the stored cells was examined by flow cytometry. For comparison, a cell preservative solution containing no divalent metal ion was also used.

1. Materials (1-1) Cell Preservative Solution

In Example 10, cell preservative solutions were prepared by mixing methanol (Wako Pure Chemical Industries, Ltd.), magnesium chloride (Kishida Chemical Co., Ltd.), and calcium chloride (Kishida Chemical Co., Ltd.) so as to have the composition shown in Table 11 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.7. The cells, reagent, and flow cytometer are the same as those used in Example 4.

TABLE 11

|  | Methanol (v/v%) | MgCl$_2$ (mmol/L) | CaCl$_2$ (mmol/L) |
|---|---|---|---|
| Cell preservative solution 65 | 43 | 0 | 0 |
| Cell preservative solution 66 | 43 | 10 | 10 |

2. Storage of Cells and FCM Analysis

HeLa cells were added to and suspended in the cell preservative solutions 65 and 66, respectively. The resulting cell suspensions were allowed to stand at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.

3. Results

Figure 14:
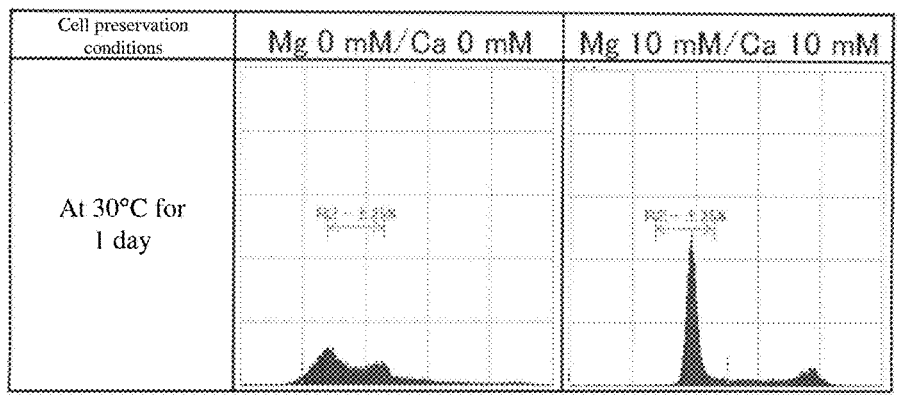
FIG. 14 shows fluorescence area histograms obtained by analyzing HeLa cells stored in a cell preservative solution containing a magnesium ion and a calcium ion under predetermined conditions with the flow cytometer.

FIG. 14 shows the created fluorescence area histograms. As shown in FIG. 14, when cells were stored in the cell preservative solution 65 containing no divalent metal ion at 30° C., the histogram shape was broken. Meanwhile, when the cell preservative solution 66 having a total concentration of divalent metal ions of 20 mmol/L was used, the histogram shape was favorable. Thus, it was shown that, by using the cell preservative solution containing two kinds of divalent metal ions at an appropriate concentration, DNA in cells could be stably maintained even when stored under the temperature condition of 30° C.

Example 11

Cells were fixed and stored in a cell preservative solution containing ethanol as the lower alcohol. The stability of DNA in the stored cells was examined by flow cytometry.

1. Materials (1-1) Cell Preservative Solution

In Example 11, cell preservative solutions were prepared by mixing ethanol (Wako Pure Chemical Industries, Ltd.) and magnesium chloride (Kishida Chemical Co., Ltd.) so as to have the composition shown in Table 12 below. In preparation of the cell preservative solutions, water was used as a solvent and PIPES (DOJINDO LABORATORIES) as a buffer was added so as to give a concentration of 20 mM. The NaOH aqueous solution was used to adjust the pH. The cell preservative solution had a pH of 6.7. The cells, reagent, and flow cytometer are the same as those used in Example 4.

TABLE 12

|  | Methanol (v/v%) | MgCl$^2$ (mmol/L) |
|---|---|---|
| Cell preservative solution 67 | 30 | 20 |

2. Storage of Cells and FCM Analysis

HeLa cells were added to and suspended in the cell preservative solution 67. The resulting cell suspension was allowed to stand at 30° C. for 7 days. A measurement sample was prepared from the cell suspension in the same manner as in Example 4. The resulting measurement sample was introduced into the flow cytometer and optical signals (a fluorescent signal and a forward scattered light signal) were obtained. Then, a fluorescence area histogram was created in the same manner as in Example 4.

3. Results

Figure 15:
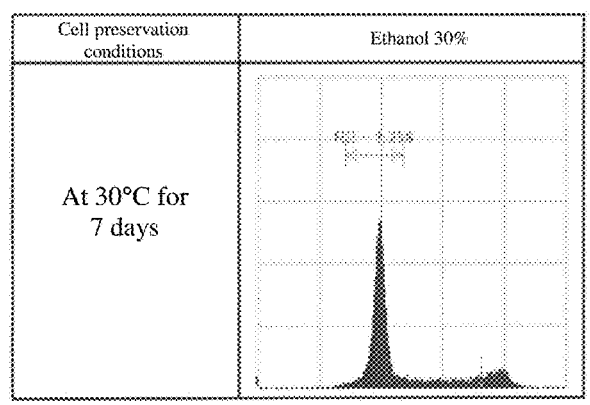
FIG. 15 is a fluorescence area histogram obtained by analyzing HeLa cells stored in a cell preservative solution containing ethanol under predetermined conditions with the flow cytometer.

FIG. 15 shows the created fluorescence area histogram. As shown in FIG. 15, when cells were stored in the cell preservative solution 67 containing ethanol as the lower alcohol, the histogram shape was favorable. Therefore, it was suggested that, using a cell preservative solution containing ethanol and a divalent metal ion at an appropriate concentration, DNA in cells could be stably maintained even when stored under the temperature condition of 30° C.

Comparative Example 2

The stability of DNA in the cells stored in the cell preservative solution of the embodiment was compared to the stability of DNA in the cells stored in the cell preservative solution described in Example 5 of Patent Literature 1 (U.S. Pat. No. 5,256,571).
1. Materials
(1-1) Cell Preservative Solution As the cell preservative solution of the embodiment, the cell preservative solution of Example 1 was used. Further, as the cell preservative solution described in Example 5 of Patent Literature 1 (hereinafter, also referred to as "cell preservative solution of Comparative Example 2"), a cell preservative solution having the following composition was prepared. The cells, reagent, and flow cytometer are the same as those used in Example 4.

Cell Preservative Solution of Comparative Example 2

Figure 16:
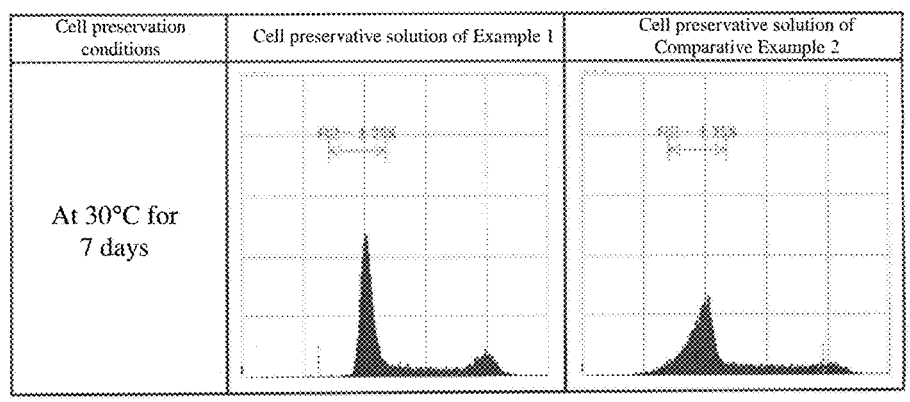
FIG. 16 shows fluorescence area histograms obtained by analyzing HeLa cells stored in the cell preservative solution of Example 1 or the cell preservative solution disclosed in U.S. Pat. No. 5,256,571 under predetermined conditions with the flow cytometer.

1 mM magnesium acetate hexahydrate
2 mM calcium acetate monohydrate
10 mM potassium chloride
0.1% sodium chloride
20% methanol
2. Storage of Cells and FCM Analysis HeLa cells were added to and suspended in the cell preservative solution of Example 1 and the cell preservative solution of Comparative Example 2, respectively. The resulting cell suspensions were allowed to stand at 30° C. for 7 days. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.
3. Results FIG. 16 shows the created fluorescence area histograms. As shown in FIG. 16, when cells were stored in the cell preservative solution of Example 1 at 30° C. for 7 days, the histogram shape in the fluorescence area was normal. Meanwhile, when cells were stored in the cell preservative solution of Comparative Example 2, the histogram shape was broken. Therefore, it is found that the cell preservative solution described in Example 5 of U.S. Pat. No. 5,256,571 is different from the cell preservative solution of the embodiment and not suitable for storage under the temperature condition of 30° C.

Example 12

Normal tissue-derived cells were fixed and stored in a cell preservative solution containing a magnesium ion. The stability of DNA in the stored cells was examined by flow cytometry.

1. Materials
(1.1) Cell Preservative Solution

In Example 12, cell preservative solutions were prepared by mixing methanol (Wako Pure Chemical Industries, Ltd.) and magnesium chloride (Kishida Chemical Co., Ltd.) so as to have the composition shown in Table 13 below. In preparation of the cell preservative solutions, water was used as a solvent and PIPES (DOJINDO LABORATORIES) as a buffer was added so as to give a concentration of 20 mM. The NaOH aqueous solution was used to adjust the pH. Each of the cell preservative solutions had a pH of 6.7.

TABLE 13

|  | Methanol (v/v%) | $MgCl_2$ (mmol/L) |
|---|---|---|
| Cell preservative solution 68 | 43 | 0 |
| Cell preservative solution 69 | 43 | 6 |
| Cell preservative solution 70 | 43 | 20 |
| Cell preservative solution 71 | 43 | 82 |

(1-2) Cells, Reagent and Flow Cytometer

Figure 17:
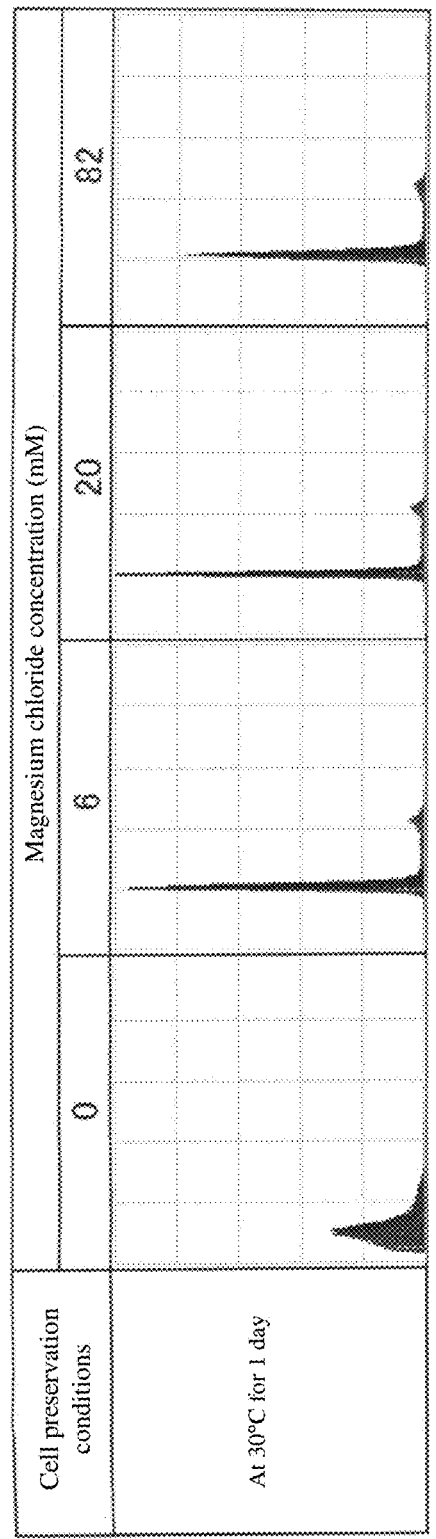
FIG. 17 shows fluorescence area histograms obtained by analyzing HUVEC cells stored in cell preservative solutions having various magnesium ion concentrations under predetermined conditions with the flow cytometer.

As normal tissue-derived cells to be stored in the cell preservative solution, human umbilical vein endothelial cell lines HUVEC (purchased from ATCC) were used. The HUVEC cells were cultured in the same manner as culturing of the HeLa cells of Example 1. The reagent and flow cytometer are the same as those used in Example 4.
2. Storage of Cells and FCM Analysis HUVEC cells were added to and suspended in the cell preservative solutions 68 to 71, respectively. The resulting cell suspensions were allowed to stand at 30° C. for 24 hours. Measurement samples were prepared from the cell suspensions in the same manner as in Example 4. Each of the resulting measurement samples was introduced into the flow cytometer and optical signals (a fluorescent signal and a forward scattered light signal) were obtained. Then, fluorescence area histograms were created in the same manner as in Example 4.
3. Results FIG. 17 shows the created fluorescence area histograms. As shown in FIG. 17, when the HUVEC cells were stored in the cell preservative solution 68 containing no magnesium ion at 30° C., the histogram shape was broken. Meanwhile, when cells were stored in cell preservative solutions 69, 70, and 71 having magnesium ion concentrations of 6, 20, and 82 mmol/L respectively at 30° C., the histogram shapes were favorable. Consequently, it was shown that, by using the cell preservative solution of the embodiment, even when normal tissue-derived cells were stored under the temperature condition of 30° C., DNA in the cells could be stably maintained.

REFERENCE SIGNS LIST

11: Cell preservative solution accommodating container

The invention claimed is:
1. A method of preserving cells, comprising contacting the cells in vitro with a cell preservative solution, wherein the cell preservative solution comprises a lower alcohol having 1 to 6 carbon atoms and a divalent metal ion in an aqueous solvent, wherein the concentration of the divalent metal ion is from about 6 mmol/L to about 82 mmol/L.
2. The method according to claim 1, wherein the divalent metal ion is a metal ion of the Group II element.

3. The method according to claim 1, wherein the divalent metal ion is at least one selected from a magnesium ion and a calcium ion.

4. The method according to claim 1, wherein the concentration of the divalent metal ion is from about 6 mmol/L to about 80 mmol/L.

5. The method according to claim 1, wherein the concentration of the divalent metal ion is from about 6 mmol/L to about 60 mmol/L.

6. The method according to claim 1, wherein the concentration of the divalent metal ion is from about 6 mmol/L to about 50 mmol/L.

7. The method according to claim 1, wherein the concentration of the divalent metal ion is from about 6 mmol/L to about 40 mmol/L.

8. The method according to claim 1, wherein the lower alcohol is at least one selected from methanol and ethanol.

9. The method according to claim 1, wherein the concentration of the lower alcohol is from about 20% by volume to about 60% by volume.

10. The method according to claim 1, wherein the pH is from about 6 to about 8.

11. The method according to claim 1, wherein cells stored in the cell preservative solution are cervical cells, cells in the uterine corpus, oral cells, mammary glandular cells, thyroid cells, cells in urine, cells in the sputum, bronchial brushing cells, cells in the peritoneal washing, or cells in the coelomic fluid, which are extracted from the living body, or cells included in the extracted tissue.

12. A method of preserving cells, comprising immersing the cells in vitro in a cell preservative solution, wherein the cell preservative solution comprises a lower alcohol having 1 to 6 carbon atoms and a divalent metal ion in an aqueous solvent, wherein the concentration of the divalent metal ion is from about 6 mmol/L to about 82 mmol/L.

13. The method according to claim 12, wherein the divalent metal ion is at least one selected from a magnesium ion and a calcium ion.

14. The method according to claim 12, wherein the concentration of the divalent metal ion is from about 6 mmol/L to about 50 mmol/L.

15. The method according to claim 12, wherein the concentration of the divalent metal ion is from about 6 mmol/L to about 40 mmol/L.

16. The method according to claim 12, wherein the lower alcohol is at least one selected from methanol and ethanol.

17. The method according to claim 12, wherein the concentration of the lower alcohol is from about 20% by volume to about 60% by volume.

18. The method according to claim 12, wherein the pH is from about 6 to about 8.

19. The method according to claim 12, wherein cells stored in the cell preservative solution are cervical cells, cells in the uterine corpus, oral cells, mammary glandular cells, thyroid cells, cells in urine, cells in the sputum, bronchial brushing cells, cells in the peritoneal washing, or cells in the coelomic fluid, which are extracted from the living body, or cells included in the extracted tissue.

20. A method of preserving cells, comprising allowing the cells to be contacted in vitro with a cell preservation solution whereby the fixed cells are prepared, wherein the cell preservative solution comprises a lower alcohol having 1 to 6 carbon atoms and a divalent metal ion in an aqueous solvent, wherein the concentration of the divalent metal ion is from about 6 mmol/L to about 82 mmol/L.

* * * * *